US008288359B2

(12) United States Patent
Klinman et al.

(10) Patent No.: US 8,288,359 B2
(45) Date of Patent: *Oct. 16, 2012

(54) METHOD OF TREATING INFLAMMATORY ARTHROPATHIES WITH SUPPRESSORS OF CPG OLIGONUCLEOTIDES

(75) Inventors: Dennis Klinman, Potomac, MD (US); Rainald Zeuner, Kiel (DE); Daniela Verthelyi, Potomac, MD (US); Ihsan Gursel, Rockville, MD (US); Mayda Gursel, Rockville, MD (US)

(73) Assignee: The Government of the United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,725

(22) Filed: Apr. 25, 2011

(65) Prior Publication Data
US 2011/0201676 A1 Aug. 18, 2011

Related U.S. Application Data

(60) Division of application No. 12/325,106, filed on Nov. 28, 2008, now Pat. No. 7,951,786, which is a continuation of application No. 10/523,273, filed as application No. PCT/US03/24205 on Jul. 31, 2003, now Pat. No. 7,514,415.

(60) Provisional application No. 60/400,826, filed on Aug. 1, 2002, provisional application No. 60/401,631, filed on Aug. 6, 2002.

(51) Int. Cl.
A61K 31/70 (2006.01)
(52) U.S. Cl. ............... 514/44 R; 536/24.3; 536/24.5; 536/23.1; 536/25.6
(58) Field of Classification Search ............... None
See application file for complete search history.

(56) References Cited

U.S. PATENT DOCUMENTS

| 4,469,863 | A | 9/1984 | Ts'o et al. |
| 5,023,243 | A | 6/1991 | Tullis |
| 5,663,153 | A | 9/1997 | Hutcherson et al. |
| 6,214,806 | B1 | 4/2001 | Krieg et al. |
| 7,094,766 | B1 | 8/2006 | Gilchrest et al. |
| 7,514,414 | B2 * | 4/2009 | Klinman et al. ............ 514/44 R |
| 7,514,415 | B2 | 4/2009 | Klinman et al. |
| 8,043,622 | B2 * | 10/2011 | Klinman et al. ........... 424/184.1 |
| 8,053,422 | B2 * | 11/2011 | Klinman et al. ............ 514/44 R |
| 2003/0087848 | A1 | 5/2003 | Bratzler et al. |
| 2004/0132682 | A1 | 7/2004 | Klinman et al. |
| 2004/0248834 | A1 | 12/2004 | Klinman et al. |
| 2006/0074039 | A1 | 4/2006 | Klinman et al. |
| 2009/0208468 | A1 | 8/2009 | Klinman et al. |
| 2011/0077289 | A1 * | 3/2011 | Klinman et al. ............ 514/44 R |

FOREIGN PATENT DOCUMENTS

| EP | 0 092 574 | 4/1992 |
| EP | 1 167 377 | 1/2002 |
| WO | WO 83/01451 | 4/1983 |
| WO | WO 95/26204 | 9/1995 |
| WO | WO 96/02555 | 2/1996 |
| WO | WO 98/11211 | 3/1998 |
| WO | WO 98/18810 | 5/1998 |
| WO | WO 98/37919 | 9/1998 |
| WO | WO 98/40100 | 9/1998 |
| WO | WO 98/52581 | 11/1998 |
| WO | WO 99/51259 | 10/1999 |
| WO | WO 03/027313 | 4/2003 |

OTHER PUBLICATIONS

Battegay, "Angiogenesis: mechanistic insignts, neovascular diseases, and therapeutic prospects," *J. Molec. Med.* 73(7): 333-346 (1995).
Beck et al., "Vascular development: cellular and molecular regulation," *FASEB J.* 11(5): 365 (1997).
Bjersing et al., "Anti-proliferative effects of phosphodiester oligodeoxynucleotides," *Immunobiology*, 209(8):637-45 (2004).
Braun et al., "On the Difficulties of Establishing a Consensus on the Definition of and Diagnostic Investigations for Reactive Arthritis," *J. Rheumatol.* 27:2185-2192 (2000).
Britigan et al., "Lactoferrin Binds CpG-Containing Oligonucleotides and Inhibits Their Immunostimulatory Effects on Human B Cells," *J. Immunol.* 167:2921-2928 (2001).
Burt et al., "Treatment of Autoimmune Disease by Intense Immunosuppressive Conditioning and Autologous Hematopoietic Stem Cell Transplantation," *Blood* 92(10):3505-3514 (Nov. 1998).
Chen et al., "Identification of methylated CpG motifs as inhibitors of the immune stimulatory CpG motifs," *Gene Ther.* 8(13):1024-1032 (2001).
Deng et al., "Intra-articularly localized bacterial DNA containing CpG motifs induces arthritis," *Nat. Med.* 5:702-705 (1999).
Deng et al., "Synovial cytokine mRNA expression during arthritis triggered by CpG motifs of bacterial DNA," *Arthritis Res.* 3(1):48-53, 2001.
Deng et al., "The Features of Arthritis Induced by CpG Motifs in Bacterial DNA," *Arthritis Rheum.* 43:356-364 (2000).
Dong et al., "Suppressive Oligodeoxynucleotides Delay the Onset of Glomerulonephritis and Prolong Survival in Lupus-Prone NZB X NZW Mice," *Arthritis & Rheumatism* 52(2):651-658 (Feb. 2005).
Dong et al., "Suppressive Oligonucleotides Protect Against Collagen-Induced Arthritis in Mice," *Arthritis & Rheumatism* 50(5):1686-1689 (May 2004).
Enokizono et al., "Structure of hnRNP D Complexed with Single-stranded Telomere DNA and Unfolding of the Quadruplex by Heterogeneous Nuclear Ribonucleoprotein D," *J. Biological Chemistry* 280(19):18862-18870 (2005).
Gaudric et al. "Quantification of Angiogenesis due to Basic Fibroblast Growth Factor in a Modified Rabbit Corneal Model," *Ophthal. Res.* 24: 181 (1992).
Gürsel et al., "Differential and competitive activiation of human immune cells by distinct classes of CpG oligodeoxynucleotide," *J. Leuko.Biol.* 71:813-820 (2002).
Gürsel et al., "Repetitive Elements in Mammalian Telomeres Suppress Bacterial DNA-Induced Immune Activation," *J. Immunology* 171:1393-1400 (2003).
Gürsel et al., "Sterically Stabilized Cationic Liposomes Improve the Uptake and Immunostimulatory Activity of CpG Oligonucleotides," *J. Immunol.* 167: 3324 (2001).
Han et al., "G-quadruplex DNA: a potential target for anti-cancer drug design," *Trends Pharmacol. Sci.* 21:136-142 (2000).
Hartmann et al., "CpG DNA: A potent signal for growth, activation, and maturation of human dendritic cells," *Proc. Natl. Acad. Sci. USA* 96:9305-9310 (1999).

(Continued)

Primary Examiner — Zachariah Lucas
Assistant Examiner — Michelle S Horning
(74) Attorney, Agent, or Firm — Klarquist Sparkman, LLP

(57) ABSTRACT

The present disclosure relates to oligodeoxynucleotides that suppress an immune response. Methods are disclosed for preventing or treating inflammatory arthropathies by administering a therapeutically effective amount of a suppressive oligodeoxynucleotide.

20 Claims, 22 Drawing Sheets

OTHER PUBLICATIONS

Ho et al., "An Immunomodulatory GpG Oligonucleotide for the Treatment of Autoimmunity via the Innate and Adaptive Immune Systems," *J. Immunol.* 171:4920-4926 (2003).

International Search Report from the prior PCT Application No. PCT Application No. PCT/US2003/024205, 3 pages (mailed on Nov. 18, 2005).

Iwakura et al., "The Development of Autoimmune Inflammatory Arthropathy in Mice Transgenic for the Human T Cell Leukemia Virus Type-1 env-pX Region is not Dependent on H-2 Haplotypes and Modified by the Expression Levels of Fas Antigen," *J. Immunology* 161:6592-6598 (1998).

Kenyon et al., "A Model of Angiogenesis in the Mouse Cornea," *Invest Opthalmol. Vis. Sci.* 37:1625-1632, (1996).

Klinman et al., "Activation of the innate immune system by CpG oligodeoxynucleotides: immunoprotective activity and safety," *Springer Semin. Immunopathol.* 22:173-183 (2000).

Klinman et al., "Contribution of CpG Motifs to the Immunogenicity of DNA Vaccines," *J.Immunol.* 158:3635-3639 (1997).

Klinman et al., "CpG Motifs present in bacterial DNA rapdily induce lymphocytes to secrete interleukin 6, interleukin 12, and interferon γ," *Proc. Natl. Acad. Sci.* USA 93:2879 (1996).

Krieg et al., "CpG motifs in bacterial DNA trigger direct B-cell activation," *Nature* 374:546-549 (1995).

Krieg et al., "Enhancing vaccines with immune stimulatory CpG DNA," *Curr Opin Mol Ther* 3(1):15-24 (2001).

Krieg et al., "Sequence motifs in adenoviral DNA block immune activation by stimulatory CpG motifs" *Proc. Natl. Acad. Sci. USA* 95:12631-12636 (1998).

Krieg, "Commentary: A possible cause of joint destruction in septic arthritis," *Arthritis Research* 1(1):3-4 (1999).

Krieg, "CpG Motifs in bacterial DNA and their immune effects," *Annu Rev Immunol* 20:709-760 (2002).

Krieg, "From A to Z on CpG," *Trends Immunol.* 23(2):64-65 (2002).

Krieg, "From bugs to drugs: therapeutic immunomodulation with oligodeoxynucleotides containing CpG sequences from bacterial DNA," *Antisense Nucleic Acid Drug Dev* 11(3):181-188 (2001).

Lenert et al., "CpG stimulation of primary mouse B cells is blocked by inhibitory oligodeoxyribonuceotides at a site proximal to NF-kappaB activation." *Antisense Nucleic Acid Drug Dev* 11(4):247-256 (2001).

Liang et al., "Activation of Human B Cells by Phosphorothioate Oligodeoxynucleotides," *J. Clin. Invest.* 98:1119-1129 (1996).

Lichtenberg et al., "The Rat Subcutaneous Air Sac Model: A Quantitative Assay of Antiangiogenesis in Induced Vessels,"*Pharmacol Toxicol.* 84:34-40 (1999).

Matsukawa et al., *Clin. Exp. Immunol.*, 93:206-211.

McCluskie et al., "Psarental and Mucosal Prime-boost Immunization Strategies in Mice with Hepatitis B Surface Antigen and CpG DNA," *FEMS Immunology and Medical Microbiology* 32:179-185 (2002).

Murchie et al., "Tetraplex folding of telomere sequences and the inclusion of adenine bases,"*EMBO J.* 13:993-1001 (1994).

Pisetsky et al., "Immunological Properties of Bacterial DNA," *NY Acad Sci.* 772:152-163 (1995).

Pisetsky et al., "Inhibition of Murine Macrophage IL-12 Production by Natural and Synthetic DNA," *Clin. Immunol.* 96, 198-204 (2000).

Quarcoo et al., "Inhibition of signal transducer and activator of transcription 1 attenuates allergen-induced airway inflammation and hyperreactivity," *J Allergy Clin Immunol.*, 114(2):288-95 (2004).

Roman et al., "Immunostimulatory DNA sequences function as T helper-1-promoting adjuvants," *Nature Medicine* 3(8):849-854 (1997).

Schnitzer and Hochberg, "cox-2-Selective Inhibitors in the treatment of Arthritis," *Cleveland Clinic Journal of Medicine* 69(1):SI-20-30 (Apr. 2002).

Schwartz, "Bacterial DNA or Oligonucleotides Containing Unmethylated CpG Motifs Can Minimize Lipopolysaccharide-Induced Inflammation in the Lower Respiratory Tract Through an IL-12-Dependent Pathway," *J. Immunol. 163*:224-231 (1999).

Schwartz, CpG Motifs in Bacterial DNA Cause Inflammation in the Lower Respiratory Tract, *J. Clin. Invest. 100*:68-73 (1997).

Shirota et al., "Suppressive Oligodeoxynucleotides Protect Mice from Lethal Endotoxic Shock," *J. Immunology* 174:4579-4583 (2005).

Stunz et al., "Inhibitory oligonucleotides specifically block effects of stimulatory CpG oligonucleotides in B cells," *Eur J Immunol* 32(5):1212-1222 (2002).

Verthelyi et al., "Human Peripheral Blood Cells Differentially Recognize and Respond to Two Distinct CpG Motifs," *J. Immunol.* 166:2372-2377 (2001).

Vialas et al., "Oxidative Damage Generated by an Oxo-Metalloporphyrin onto the Human Telomeric Sequence," *Biochemistry* 39:9514-9522 (2000).

Wilting et al., "A modified chorioallantoic membrane (CAM) assay for qualitative and quantitative study of growth factors," *Anat. Embryol.* 183: 259-271 (1991).

Yamada et al., "Effect of Suppressive DNA on CpG-Induced Immunce Activation," *J. Immunol.* 169:5590-5594 (2002).

Yamamoto et al., "Unique Pallindromic Sequences in Synthetic Oligonucleotides are Required to Induce INF and Augment INF-Mediated Natural Killer Activity," *J. Immunol.* 148:4072-4076 (1992).

Yi et al., "Rapid Immune Activation by CpG Motifs in Bacterial DNA," *J. Immun.* 157:5394-5402 (1996).

Zeuner et al., "Reduction of CpG-induced arthritis by suppressive oligodeoxynucleotides," *Arthritis Rheum.* 46(8):2219-2224 (2002).

Zhao et al., "Requirements for effective inhibition of immunostimulatory CpG motifs by neutralizing motifs," *Antisense Nucleic Acid Drug Dev.* 10(5):381-389 (2000).

Zheng et al., "DNA containing CpG motifs induces angiogenesis," *PNAS* 99(13):8944-8949 (2002).

Zeuner et al., "Influence of Stimulatory and Suppressive DNA Motifs on Host Susceptibility to Inflammatory Arthritis," Arthritis and Rheumatism, 48(6), 1701-1707, (Jun. 2003).

\* cited by examiner a Mammalian DNA suppresses CpG DNA induced immune activation
Bacterial DNA
Mammalian DNA
Bacterial DNA + Mammalian DNA
CpG ODN
CpG ODN + Bacterial DNA
CpG ODN + Mammalian DNA

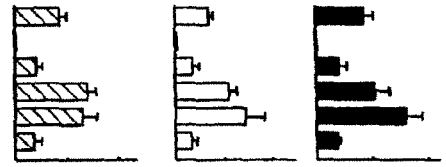

b Telomeric TTAGGG repetitive motif is suppressive

|  | Ellipticity (mdeg/abs) |
|---|---|
| CpG ODN | 1.4 |
| CpG ODN + (TTAGGG)$_4$ | 7.1 |
| CpG ODN + (TTAGGG)$_3$ | 4.8 |
| CpG ODN + (TTAGGG)$_2$ | 2.6 |
| CpG ODN + (TTAGGG)$_1$ | 1.2 |
| CpG ODN + TCAACCTTCATTAGGG | 3.4 |
| CpG ODN + TTAGGGTCAACCTTCA | 3.4 |

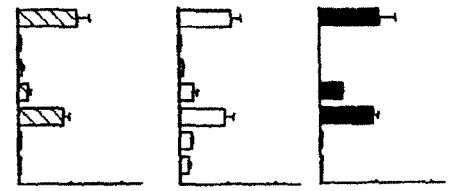

c Suppressive motif is active in *trans* and *cis*
Trans
CpG ODN
CpG ODN + Control ODN
CpG ODN + Suppressive ODN
Cis
(Control-CpG) ODN
(Suppressive-CpG) ODN
(Control-CpG) ODN + CpG ODN
(Suppressive-CpG) ODN + CpG ODN

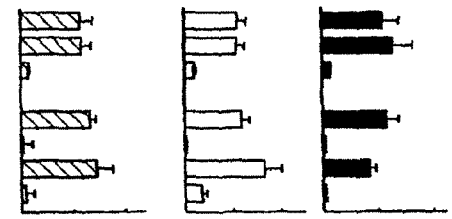

d Suppressive ODN selectively block CpG DNA induced immune activation
CpG ODN
CpG ODN + Suppressive ODN
Bacterial DNA
Bacterial DNA + Suppressive ODN
LPS
LPS + Suppressive ODN

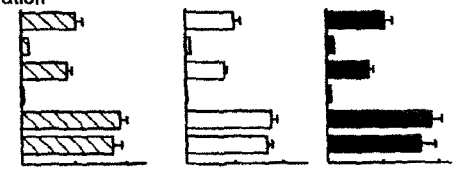

e Poly G's are critical for suppression

| | | |
|---|---|---|
| CpG ODN | | 1.4 |
| CpG ODN + | T T A G G G T C A A C C T T C A | 3.4 |
| CpG ODN + | – A C – – – – – – – – – – – – – | |
| CpG ODN + | A C T – – – – – – – – – – – – – | |
| CpG ODN + | A A T – – – – – – – – – – – – – | |
| CpG ODN + | – – – – A A – – – – – – – – – – | |
| CpG ODN + | – – – T T – – – – – – – – – – – | |
| CpG ODN + | – – – $^7$G – – – – – – – – – – – | 1.2 |
| CpG ODN + | – – – $^7$G$^7$G – – – – – – – – – | 1.0 |
| CpG ODN + | – – – $^7$G$^7$G$^7$G – – – – – – – | 0.8 |

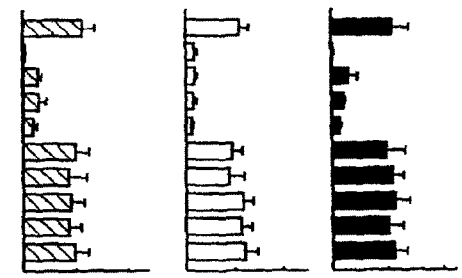

f G-tetrad forming non-telomere sequences are also suppressive

| | |
|---|---|
| CpG ODN | 1.4 |
| CpG ODN + GGGTGGGTGGGTATTACCATTA | 4.9 |
| CpG ODN + TGGGCGGTTCAACCTTCA | 4.1 |
| CpG ODN + CCTCAAGCTTGAGGGG | 4.6 |
| CpG ODN + CCGGCCGGCCGGCCGG | 2.8 |
| CpG ODN + TTGGTTGGTTGGTTGG | 3.2 |

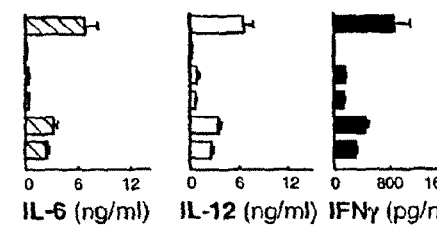

0  6  12    0  6  12    0  800 1600
IL-6 (ng/ml)  IL-12 (ng/ml)  IFNγ (pg/ml)

FIG. 10

```
SEQUENCE LISTING

<160> NUMBER OF SEQ ID NOS: 126

<210> SEQ ID NO 1
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 1
cctcaagctt gagggg                                                   16

<210> SEQ ID NO 2
<211> LENGTH: 24
<212> TYPE: DNA
<213> ORGANISM: Artificial Sequence
<220> FEATURE:
<223> OTHER INFORMATION: Suppressive oligonucleotide

<400> SEQUENCE: 2
ttagggttag ggttagggtt aggg                                          24

<210> SEQ ID NO 3
<211> LENGTH: 18
<212> TYPE: DNA
<213> ORGANISM: Artificial Sequence
<220> FEATURE:
<223> OTHER INFORMATION: Suppressive oligonucleotide

<400> SEQUENCE: 3
ttagggttag ggttaggg                                                 18

<210> SEQ ID NO 4
<211> LENGTH: 12
<212> TYPE: DNA
<213> ORGANISM: Artificial Sequence
<220> FEATURE:
<223> OTHER INFORMATION: Suppressive oligonucleotide

<400> SEQUENCE: 4
ttagggttag gg                                                       12

<210> SEQ ID NO 5
<211> LENGTH: 24
<212> TYPE: DNA
<213> ORGANISM: Artificial Sequence
<220> FEATURE:
```

```
<223> OTHER INFORMATION: Suppressive oligonucleotide

<400> SEQUENCE: 5
tgggcggttg ggcggttggg cggt                                              24

<210> SEQ ID NO 6
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 6
tgggcggttg ggcggt                                                       16

<210> SEQ ID NO 7
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 7
tcaaccttca ttaggg                                                       16

<210> SEQ ID NO 8
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 8
ttagggttag ggtcaacctt ca                                                22

<210> SEQ ID NO 9
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 9
tcaaccttca ttagggttag gg                                                22

<210> SEQ ID NO 10
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 10
gggttagggt tatcaacctt ca                                                22

<210> SEQ ID NO 11
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 11
tcaaccttca gggttagggt ta                                                22

<210> SEQ ID NO 12
```

```
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 12
gggtgggtgg gtattaccat ta                                          22

<210> SEQ ID NO 13
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 13
attaccatta gggtgggtgg gt                                          22

<210> SEQ ID NO 14
<211> LENGTH: 18
<212> TYPE: DNA
<213> ORGANISM: Artificial Sequence
<220> FEATURE:
<223> OTHER INFORMATION: Suppressive oligonucleotide

<400> SEQUENCE: 14
tgggcggttc aagcttga                                               18

<210> SEQ ID NO 15
<211> LENGTH: 18
<212> TYPE: DNA
<213> ORGANISM: Artificial Sequence
<220> FEATURE:
<223> OTHER INFORMATION: Suppressive oligonucleotide

<400> SEQUENCE: 15
tcaagcttca tgggcggt                                               18

<210> SEQ ID NO 16
<211> LENGTH: 22
<212> TYPE: DNA
<213> ORGANISM: Artificial Sequence
<220> FEATURE:
<223> OTHER INFORMATION: Suppressive oligonucleotide

<400> SEQUENCE: 16
gggtgggtgg gtagacgtta cc                                          22

<210> SEQ ID NO 17
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 17 gggggggtcaa gcttca                                                16

<210> SEQ ID NO 18
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 18
```

```
tcaagcttca gggggg                                                          16

<210> SEQ ID NO 19
<211> LENGTH: 16
<212> TYPE: DNA
<213> ORGANISM: Artificial Sequence
<220> FEATURE:
<223> OTHER INFORMATION: Suppressive oligonucleotide

<400> SEQUENCE: 19 gggggggtcaa cgttca                                                         16

<210> SEQ ID NO 20
<211> LENGTH: 20
<212> TYPE: DNA
<213> ORGANISM: Artificial Sequence
<220> FEATURE:
<223> OTHER INFORMATION: Suppressive oligonucleotide

<400> SEQUENCE: 20
gagcaagctg gaccttccat                                                      20

<210> SEQ ID NO 21
<211> LENGTH: 21
<212> TYPE: DNA
<213> ORGANISM: Artificial Sequence
<220> FEATURE:
<223> OTHER INFORMATION: Suppressive oligonucleotide

<400> SEQUENCE: 21
gagcaagctg gtagacgtta g                                                    21

<210> SEQ ID NO 22
<211> LENGTH: 20
<212> TYPE: DNA
<213> ORGANISM: Artificial Sequence
<220> FEATURE:
<223> OTHER INFORMATION: Suppressive oligonucleotide

<400> SEQUENCE: 22
gggcaagctg gacctggggg                                                      20

<210> SEQ ID NO 23
<211> LENGTH: 20
<212> TYPE: DNA
<213> ORGANISM: Artificial Sequence
<220> FEATURE:
<223> OTHER INFORMATION: Suppressive oligonucleotide

<400> SEQUENCE: 23
ggggaagctg gacctggggg                                                      20

<210> SEQ ID NO 24
<211> LENGTH: 20
<212> TYPE: DNA
<213> ORGANISM: Artificial Sequence
<220> FEATURE:
<223> OTHER INFORMATION: Suppressive oligonucleotide

<400> SEQUENCE: 24
gggcaagctg gaccttcggg                                                      20

<210> SEQ ID NO 25
<211> LENGTH: 22
<212> TYPE: DNA
<213> ORGANISM: Artificial Sequence
<220> FEATURE:
```

-continued

```
<223> OTHER INFORMATION: Suppressive oligonucleotide

<400> SEQUENCE: 25
ggcaagctgg accttcgggg gg                                            22

<210> SEQ ID NO 26
<211> LENGTH: 10
<212> TYPE: DNA
<213> ORGANISM: Artificial Sequence
<220> FEATURE:
<223> OTHER INFORMATION: Immunostimulatory oligonucleotide

<400> SEQUENCE: 26
tcaacgttga                                                          10

<210> SEQ ID NO 27
<211> LENGTH: 15
<212> TYPE: DNA
<213> ORGANISM: Artificial Sequence
<220> FEATURE:
<223> OTHER INFORMATION: Immunostimulatory oligonucleotide

<400> SEQUENCE: 27
gctagacgtt agcgt                                                    15

<210> SEQ ID NO 28
<211> LENGTH: 10
<212> TYPE: DNA
<213> ORGANISM: Artificial Sequence
<220> FEATURE:
<223> OTHER INFORMATION: Control oligonucleotide

<400> SEQUENCE: 28
tcaagcttga                                                          10

<210> SEQ ID NO 29
<211> LENGTH: 15
<212> TYPE: DNA
<213> ORGANISM: Artificial Sequence
<220> FEATURE:
<223> OTHER INFORMATION: Control oligonucleotide

<400> SEQUENCE: 29
gctagagctt aggct                                                    15

<210> SEQ ID NO 30
<211> LENGTH: 15
<212> TYPE: DNA
<213> ORGANISM: Artificial Sequence
<220> FEATURE:
<223> OTHER INFORMATION: Immunostimulatory oligonucleotide

<400> SEQUENCE: 30
gctagacgtt agcgt                                                    15

<210> SEQ ID NO 31
<211> LENGTH: 15
<212> TYPE: DNA
<213> ORGANISM: Artificial Sequence
<220> FEATURE:
<223> OTHER INFORMATION: Control oligonucleotide

<400> SEQUENCE: 31
gctagatgtt agcgt                                                    15

<210> SEQ ID NO 32
```

```
<211> LENGTH: 21
<212> TYPE: DNA
<213> ORGANISM: Artificial sequence
<220> FEATURE:
<223> OTHER INFORMATION: primer

<400> SEQUENCE: 32
atgagcacag aaagcatgat c                                              21

<210> SEQ ID NO 33
<211> LENGTH: 21
<212> TYPE: DNA
<213> ORGANISM: Artificial sequence
<220> FEATURE:
<223> OTHER INFORMATION: primer

<400> SEQUENCE: 33
tacaggcttg tcactcgaat t                                              21

<210> SEQ ID NO 34
<211> LENGTH: 24
<212> TYPE: DNA
<213> ORGANISM: Artificial sequence
<220> FEATURE:
<223> OTHER INFORMATION: primer

<400> SEQUENCE: 34
gacatggagg agtctggcac caca                                           24

<210> SEQ ID NO 35
<211> LENGTH: 25
<212> TYPE: DNA
<213> ORGANISM: Artificial sequence
<220> FEATURE:
<223> OTHER INFORMATION: primer

<400> SEQUENCE: 35
atctcctgct cgaagtctag agcaa                                          25

<210> SEQ ID NO 36
<211> LENGTH: 16
<212> TYPE: DNA
<213> ORGANISM: Artificial sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 36
nnnrycgryn nnggggg                                                   16

<210> SEQ ID NO 37
<211> LENGTH: 17
<212> TYPE: DNA
<213> ORGANISM: Artificial sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
```

<223> OTHER INFORMATION: n is a, c, g, or t

<400> SEQUENCE: 37
nnnrycgryn nnngggg        17

<210> SEQ ID NO 38
<211> LENGTH: 18
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 38
nnnrycgryn nnnngggg        18

<210> SEQ ID NO 39
<211> LENGTH: 19
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 39
nnnrycgryn nnnnngggg        19

<210> SEQ ID NO 40
<211> LENGTH: 20
<212> TYPE: DNA
<213> ORGANISM: Artificial sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 40
nnnrycgryn nnnnnngggg        20

<210> SEQ ID NO 41
<211> LENGTH: 21
<212> TYPE: DNA
<213> ORGANISM: Artificial sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)

<223> OTHER INFORMATION: n is a, c, g, or t

<400> SEQUENCE: 41
nnnrycgryn nnnnnnnggg g         21

<210> SEQ ID NO 42
<211> LENGTH: 22
<212> TYPE: DNA
<213> ORGANISM: Artificial sequence
<220> FEATURE:
<223> OTHER INFORMATION: Synthetic oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 42
nnnrycgryn nnnnnnnngg gg         22

<210> SEQ ID NO 43
<211> LENGTH: 23
<212> TYPE: DNA
<213> ORGANISM: Artificial sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 43
nnnrycgryn nnnnnnnnng ggg         23

<210> SEQ ID NO 44
<211> LENGTH: 24
<212> TYPE: DNA
<213> ORGANISM: Artificial sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 44
nnnrycgryn nnnnnnnnnn gggg         24

<210> SEQ ID NO 45
<211> LENGTH: 25
<212> TYPE: DNA
<213> ORGANISM: Artificial sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)

<223> OTHER INFORMATION: n is a, c, g, or t

<400> SEQUENCE: 45
nnnrycgryn nnnnnnnnnn ngggg                                                25

<210> SEQ ID NO 46
<211> LENGTH: 26
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 46
nnnrycgryn nnnnnnnnnn nnggggg                                              26

<210> SEQ ID NO 47
<211> LENGTH: 17
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 47
nnnrycgryn nnggggg                                                         17

<210> SEQ ID NO 48
<211> LENGTH: 18
<212> TYPE: DNA
<213> ORGANISM: Artificial sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 48
nnnrycgryn nnnggggg                                                        18

<210> SEQ ID NO 49
<211> LENGTH: 19
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)

-continued

<223> OTHER INFORMATION: n is a, c, g, or t

<400> SEQUENCE: 49
nnnrycgryn nnnnggggg                                                     19

<210> SEQ ID NO 50
<211> LENGTH: 20
<212> TYPE: DNA
<213> ORGANISM: Artificial Sequence
<220> FEATURE:
<223> OTHER INFORMATION: Sythetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 50
nnnrycgryn nnnnngggg                                                     20

<210> SEQ ID NO 51
<211> LENGTH: 21
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 51
nnnrycgryn nnnnnngggg g                                                  21

<210> SEQ ID NO 52
<211> LENGTH: 22
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 52
nnnrycgryn nnnnnnnggg gg                                                 22

<210> SEQ ID NO 53
<211> LENGTH: 23
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)

<223> OTHER INFORMATION: n is a, c, g, or t

<400> SEQUENCE: 53
nnnrycgryn nnnnnnnngg ggg                                    23

<210> SEQ ID NO 54
<211> LENGTH: 24
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 54
nnnrycgryn nnnnnnnnng gggg                                   24

<210> SEQ ID NO 55
<211> LENGTH: 25
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 55
nnnrycgryn nnnnnnnnnn ggggg                                  25

<210> SEQ ID NO 56
<211> LENGTH: 26
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 56
nnnrycgryn nnnnnnnnnn nggggg                                 26

<210> SEQ ID NO 57
<211> LENGTH: 27
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)

<223> OTHER INFORMATION: n is a, c, g, or t

<400> SEQUENCE: 57
nnnrycgryn nnnnnnnnnn nnggggg                                              27

<210> SEQ ID NO 58
<211> LENGTH: 18
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 58
nnnrycgryn nngggggg                                                        18

<210> SEQ ID NO 59
<211> LENGTH: 19
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 59
nnnrycgryn nnnggggggg                                                      19

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 60
nnnrycgryn nnnngggggg                                                      20

<210> SEQ ID NO 61
<211> LENGTH: 21
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)

-continued

<223> OTHER INFORMATION: n is a, c, g, or t

<400> SEQUENCE: 61
nnnrycgryn nnnnngggg g        21

<210> SEQ ID NO 62
<211> LENGTH: 22
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 62
nnnrycgryn nnnnnngggg gg        22

<210> SEQ ID NO 63
<211> LENGTH: 23
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 63
nnnrycgryn nnnnnnnggg ggg        23

<210> SEQ ID NO 64
<211> LENGTH: 24
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 64
nnnrycgryn nnnnnnnngg gggg        24

<210> SEQ ID NO 65
<211> LENGTH: 25
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)

<223> OTHER INFORMATION: n is a, c, g, or t

<400> SEQUENCE: 65
nnnrycgryn nnnnnnnnng ggggg                                                                                       25

<210> SEQ ID NO 66
<211> LENGTH: 26
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 66
nnnrycgryn nnnnnnnnnn gggggg                                                                                      26

<210> SEQ ID NO 67
<211> LENGTH: 27
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 67
nnnrycgryn nnnnnnnnnn nggggg                                                                                      27

<210> SEQ ID NO 68
<211> LENGTH: 28
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 68
nnnrycgryn nnnnnnnnnn nnggggg                                                                                     28

<210> SEQ ID NO 69
<211> LENGTH: 19
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)

<223> OTHER INFORMATION: n is a, c, g, or t

<400> SEQUENCE: 69
nnnrycgryn nnggggggg                                              19

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 70
nnnrycgryn nnngggggggg                                            20

<210> SEQ ID NO 71
<211> LENGTH: 21
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 71
nnnrycgryn nnnnggggg g                                            21

<210> SEQ ID NO 72
<211> LENGTH: 22
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 72
nnnrycgryn nnnnnggggg gg                                          22

<210> SEQ ID NO 73
<211> LENGTH: 23
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)

```
<223> OTHER INFORMATION: n is a, c, g, or t

<400> SEQUENCE: 73
nnnrycgryn nnnnnngggg ggg                                             23

<210> SEQ ID NO 74
<211> LENGTH: 24
<212> TYPE: DNA
<213> ORGANISM: Artificial sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 74
nnnrycgryn nnnnnnnggg gggg                                            24

<210> SEQ ID NO 75
<211> LENGTH: 25
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 75
nnnrycgryn nnnnnnnngg ggggg                                           25

<210> SEQ ID NO 76
<211> LENGTH: 26
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 76
nnnrycgryn nnnnnnnnng gggggg                                          26

<210> SEQ ID NO 77
<211> LENGTH: 27
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
```

<223> OTHER INFORMATION: n is a, c, g, or t

<400> SEQUENCE: 77
nnnrycgryn nnnnnnnnnn ggggggg                                                    27

<210> SEQ ID NO 78
<211> LENGTH: 28
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 78
nnnrycgryn nnnnnnnnnn nggggggg                                                   28

<210> SEQ ID NO 79
<211> LENGTH: 29
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 79
nnnrycgryn nnnnnnnnnn nnggggggg                                                  29

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 80
nnnrycgryn nnggggggggg                                                           20

<210> SEQ ID NO 81
<211> LENGTH: 21
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)

<223> OTHER INFORMATION: n is a, c, g, or t

<400> SEQUENCE: 81
nnnrycgryn nnngggggg g                                             21

<210> SEQ ID NO 82
<211> LENGTH: 22
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 82
nnnrycgryn nnnngggggg gg                                           22

<210> SEQ ID NO 83
<211> LENGTH: 23
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 83
nnnrycgryn nnnnnggggg ggg                                          23

<210> SEQ ID NO 84
<211> LENGTH: 24
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 84
nnnrycgryn nnnnnnggggg gggg                                        24

<210> SEQ ID NO 85
<211> LENGTH: 25
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)

<223> OTHER INFORMATION: n is a, c, g, or t

<400> SEQUENCE: 85
nnnrycgryn nnnnnnnggg ggggg    25

<210> SEQ ID NO 86
<211> LENGTH: 26
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 86
nnnrycgryn nnnnnnnngg gggggg    26

<210> SEQ ID NO 87
<211> LENGTH: 27
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 87
nnnrycgryn nnnnnnnnng ggggggg    27

<210> SEQ ID NO 88
<211> LENGTH: 28
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 88
nnnrycgryn nnnnnnnnnn gggggggg    28

<210> SEQ ID NO 89
<211> LENGTH: 29
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)

<223> OTHER INFORMATION: n is a, c, g, or t

<400> SEQUENCE: 89
nnnrycgryn nnnnnnnnnn nggggggggg                                    29

<210> SEQ ID NO 90
<211> LENGTH: 30
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 90
nnnrycgryn nnnnnnnnnn nnggggggggg                                   30

<210> SEQ ID NO 91
<211> LENGTH: 21
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 91
nnnrycgryn nngggggggg g                                             21

<210> SEQ ID NO 92
<211> LENGTH: 22
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 92
nnnrycgryn nnnggggggg gg                                            22

<210> SEQ ID NO 93
<211> LENGTH: 23
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)

<223> OTHER INFORMATION: n is a, c, g, or t

<400> SEQUENCE: 93
nnnrycgryn nnnnggggg ggg                                           23

<210> SEQ ID NO 94
<211> LENGTH: 24
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 94
nnnrycgryn nnnnnggggg gggg                                         24

<210> SEQ ID NO 95
<211> LENGTH: 25
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 95
nnnrycgryn nnnnnngggg ggggg                                        25

<210> SEQ ID NO 96
<211> LENGTH: 26
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 96
nnnrycgryn nnnnnnnggg gggggg                                       26

<210> SEQ ID NO 97
<211> LENGTH: 27
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)

<223> OTHER INFORMATION: n is a, c, g, or t

<400> SEQUENCE: 97
nnnrycgryn nnnnnnnngg ggggggg       27

<210> SEQ ID NO 98
<211> LENGTH: 28
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 98
nnnrycgryn nnnnnnnnng ggggggg       28

<210> SEQ ID NO 99
<211> LENGTH: 29
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 99
nnnrycgryn nnnnnnnnnn ggggggggg      29

<210> SEQ ID NO 100
<211> LENGTH: 30
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 100
nnnrycgryn nnnnnnnnnn nggggggggg     30

<210> SEQ ID NO 101
<211> LENGTH: 31
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)

-continued

<223> OTHER INFORMATION: n is a, c, g, or t

<400> SEQUENCE: 101
nnnrycgryn nnnnnnnnnn nnggggggggg g         31

<210> SEQ ID NO 102
<211> LENGTH: 22
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 102
nnnrycgryn nngggggggg gg         22

<210> SEQ ID NO 103
<211> LENGTH: 23
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 103
nnnrycgryn nnnggggggg ggg         23

<210> SEQ ID NO 104
<211> LENGTH: 24
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 104
nnnrycgryn nnnngggggg gggg         24

<210> SEQ ID NO 105
<211> LENGTH: 25
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)

<223> OTHER INFORMATION: n is a, c, g, or t

<400> SEQUENCE: 105
nnnrycgryn nnnnnggggg ggggg                25

<210> SEQ ID NO 106
<211> LENGTH: 26
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 106
nnnrycgryn nnnnnnggggg gggggg                26

<210> SEQ ID NO 107
<211> LENGTH: 27
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 107
nnnrycgryn nnnnnnnggg ggggggg                27

<210> SEQ ID NO 108
<211> LENGTH: 28
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 108
nnnrycgryn nnnnnnnngg gggggggg                28

<210> SEQ ID NO 109
<211> LENGTH: 29
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)

<223> OTHER INFORMATION: n is a, c, g, or t

<400> SEQUENCE: 109
nnnrycgryn nnnnnnnnng gggggggggg    29

<210> SEQ ID NO 110
<211> LENGTH: 30
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 110
nnnrycgryn nnnnnnnnnn gggggggggg    30

<210> SEQ ID NO 111
<211> LENGTH: 31
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 111
nnnrycgryn nnnnnnnnnn nggggggggg g    31

<210> SEQ ID NO 112
<211> LENGTH: 32
<212> TYPE: DNA
<213> ORGANISM: Artificial Sequence
<220> FEATURE:
<223> OTHER INFORMATION: Synthetic Oligodeoxynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 112
nnnrycgryn nnnnnnnnnn nnggggggggg gg    32

<210> SEQ ID NO 113
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 113
tcaaccttca ttaggg    16

<210> SEQ ID NO 114

```
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 114
ttagggtcaa ccttca                                                    16

<210> SEQ ID NO 115
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 115
tacgggtcaa ccttca                                                    16

<210> SEQ ID NO 116
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 116
actgggtcaa ccttca                                                    16

<210> SEQ ID NO 117
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 117
aatgggtcaa ccttca                                                    16

<210> SEQ ID NO 118
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 118
ttagaatcaa ccttca                                                    16

<210> SEQ ID NO 119
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 119
ttattgtcaa ccttca                                                    16

<210> SEQ ID NO 120
<211> LENGTH: 22
<212> TYPE: DNA
<213> ORGANISM: Artificial sequence
<220> FEATURE:
<223> OTHER INFORMATION: Suppressive oligonucleotide

<400> SEQUENCE: 120
``` ttagggggggg ggtcaaccttt ca                                          22

<210> SEQ ID NO 121
<211> LENGTH: 28
<212> TYPE: DNA
<213> ORGANISM: Artificial sequence
<220> FEATURE:
<223> OTHER INFORMATION: Suppressive oligonucleotide

<400> SEQUENCE: 121 ttagggggggg ggggggggtc aaccttca                                     28

<210> SEQ ID NO 122
<211> LENGTH: 34
<212> TYPE: DNA
<213> ORGANISM: Artificial sequence
<220> FEATURE:
<223> OTHER INFORMATION: Suppressive oligonucleotide

<400> SEQUENCE: 122 ttagggggggg gggggggggg ggggtcaacc ttca                              34

<210> SEQ ID NO 123
<211> LENGTH: 18
<212> TYPE: DNA
<213> ORGANISM: Artificial sequence
<220> FEATURE:
<223> OTHER INFORMATION: Suppressive oligonucleotide

<400> SEQUENCE: 123
tgggcggttc aaccttca                                                 18

<210> SEQ ID NO 124
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 124
cctcaagctt gagggg                                                   16

<210> SEQ ID NO 125
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 125
ccggccggcc ggccgg                                                   16

<210> SEQ ID NO 126
<211> LENGTH: 16
<212> TYPE: DNA
<213> ORGANISM: Artificial sequence
<220> FEATURE:
<223> OTHER INFORMATION: Suppressive oligonucleotide

<400> SEQUENCE: 126
ttggttggtt ggttgg                                                   16

METHOD OF TREATING INFLAMMATORY ARTHROPATHIES WITH SUPPRESSORS OF CPG OLIGONUCLEOTIDES

CROSS REFERENCE TO RELATED APPLICATIONS

This is a divisional of U.S. patent application Ser. No. 12/325,106, filed on Nov. 28, 2008, issued as U.S. Pat. No. 7,951,786, which is a continuation of U.S. patent application Ser. No. 10/523,273, filed on Jan. 31, 2005, issued as U.S. Pat. No. 7,514,415. U.S. patent application Ser. No. 10/523,273 is the § 371 U.S. National Stage of International Application No. PCT/US2003/024205, filed Jul. 31, 2003, which was published in English under PCT Article 21(2), which in turn claims the benefit of U.S. Provisional Patent Application No. 60/400,826, filed Aug. 1, 2002, and to U.S. Provisional Patent Application No. 60/401,631, filed Aug. 6, 2002. All of the prior applications are incorporated herein by reference in their entirety.

FIELD OF THE DISCLOSURE

The present disclosure relates to oligodeoxynucleotides that suppress an immune response to CpG oligodeoxynucleotides, and to the use of these suppressors in preventing or treating inflammatory arthropathies.

BACKGROUND

Arthritis, an inflammatory disease that affects the synovial membranes of one or more joints in the body, is the most common type of joint disease. Billions of dollars are spent annually for the treatment of arthritis and for lost days of work associated with the disease. The disease is usually oligoarticular (affects few joints), but may be generalized. The joints commonly involved include the hips, knees, lower lumbar and cervical vertebrae, proximal and distal interphangeal joints of the fingers, first carpometacarpal joints, and first tarsometatarsal joints of the feet.

One type of arthritis is reactive arthritis, which is an acute nonpurulent arthritis secondary to a urinary tract or gastrointestinal infection with a variety of microorganisms, including *Chlamydia trachomatis, Yersinia, Salmonella, Shigella*, and *Campylobacter*. Microbial components (and not live organisms) are found in the affected joints. The arthritis appears abruptly and tends to involve the knees and ankles, but sometimes involves the wrists, fingers, and/or toes. Untreated, the arthritis lasts for about a year, then generally abates and only rarely is accompanied by ankylosing spondylitis. Despite evidence of disease being triggered by bacterial infection, viable bacteria are rarely present in affected joints and antibiotic treatment seldom provides relief.

Up to 16% of subjects with gastrointestinal (GI) infection by *Salmonella* or *Shigella* subsequently develop arthritis. Despite this temporal association, it is unclear whether live bacteria reaching the affected joint are the cause of this arthritis. To date, success in culturing viable microorganisms from the affect joints has been quite limited, and antibiotic treatment rarely is of benefit. Symptomatic treatment is often accomplished with high doses of non-steroidal anti-inflammatory agents. In addition, intra-articluar steroid injections are of use. However, a need remains for additional therapies for this disease.

Rheumatoid Arthritis (RA) is a chronic, systemic, inflammatory disease that affects the synovial membranes of multiple joints. RA considered an acquired autoimmune disease, and genetic factors appear to play a role in its development. In most cases of RA, the subject has remissions and exacerbations of the symptoms. Rarely does the disease resolve completely, although at times the symptoms might temporarily remit.

Symptomatic medications, such as non-steroidal anti-inflammatory agents and aspirin, analgesics, and glucocorticoids, are used in the treatment of rheumatoid arthritis to help reduce joint pain, stiffness and swelling. In addition, low doses of methotrexate, leflunomide, D-Penicillamine, sulfasalazine, gold therapy, minocycline, azathioprine, hydroxychloroquine (and other anti-malarials), and cyclosporine are used to modify the progression of the disease. However, a need still remains for other agents that can be used to alter the progression, or ameliorate the symptoms, of this disease.

In view of the above, there exists a need for new therapies to treat inflammatory arthropathies, particularly agents that suppress the inflammation associated with arthritis

BRIEF SUMMARY OF SPECIFIC EMBODIMENTS

Disclosed herein are oligodeoxynucleotides that can be used to suppress immune activation. These suppressive oligodeoxynucleotides are of use in preventing and/or treating inflammatory arthropathies, such as, but not limited to, reactive arthritis and rheumatoid arthritis. The suppressive oligodeoxynucleotides can be administered locally or systemically. One specific, non-limiting example of local administration is by intra-articular injection. A substantially pure or isolated oligodeoxynucleotide (ODN) is disclosed herein that is at least about 8 nucleotides in length, forms a G tetrad, has a CD value of greater than 2.9, has at least two guanosines, and suppresses an immune response.

Optionally, the suppressive ODN has multiple guanosine-rich sequences, and in some examples, the ODN has one or more TTAGGG motifs. Furthermore, in particular embodiments, the ODN is modified to prevent degradation or is part of an oligodeoxynucleotide delivery complex that includes a targeting moiety. In one specific, non-limiting example the suppressive ODN suppresses CpG-DNA-induced immune activation. Also disclosed herein is a pharmacological composition that includes the suppressive ODN and a pharmacologically acceptable carrier.

A method is disclosed herein for treating or preventing an inflammatory arthropathy in a subject. The method includes administering a therapeutically effective amount of the suppressive ODN to a subject having or at risk of developing an inflammatory arthropathy, thereby treating or preventing the inflammatory arthropathy.

In another embodiment, a method of treating or preventing an inflammatory arthropathy in a subject that includes contacting immune cells with the suppressive ODN in vitro. The immune cells are and transferred to a subject having or at risk of developing an inflammatory arthropathy.

Also described herein is a kit for treating or preventing inflammatory arthropathies in a subject that includes the suppressive ODN and instructions for administering the ODN to a subject.

BRIEF DESCRIPTION OF THE FIGURES

FIG. 1A is a diagram of the structure of an individual G-tetrad that shows the Hoogsteen base pairing. $M^+$ represents a monovalent cation such as $K^+$ or $Na^+$ and dR is the sugar-phosphate backbone.
FIG. 1B is a schematic representation showing the possible folded intramolecular quadruplex structure.
FIG. 1C is a schematic showing the GG-base pair formed by means of Hoogsteen hydrogen bonds.
FIG. 1D is a schematic of an intramolecular hairpin.

FIG. 2A is a graph of joint swelling in mice treated with CpG ODN (solid circle), CpG plus control ODN (solid square), CpG plus suppressive ODN (open diamond), control ODN (open triangle), suppressive ODN (inverted open triangle), or PBS (open square, N=8-11 mice/group). FIG. 2B is a graph showing histologic changes in the injected knees. Knees were evaluated four days after treatment by a blinded investigator. Scale: 0; no inflammation, 1; sparse, localized perivascular infiltrate, 2; moderate infiltrate, 3; moderate—dense infiltrate with synovial hyperplasia. FIG. 2C is a graph showing that suppressive ODNs suppress joint swelling. At T=0, both knees were injected with 25 µg of CpG ODN. The right knee was then injected with PBS and the left knee with 25 µg of suppressive ODN either 0 (solid circles, N=3), 24 (solid squares, N=6) or 48 (solid triangles, N=6) hours later. Results show the difference in swelling between the two knees. Statistical significance was assessed by repeated-measures ANOVA using the Proc Mixed procedure (FIG. 2A, 2C) and Wilcoxon Rank sum test (B). The asterisk (*) indicates that $p<0.05$.

FIGS. 3A, 3C, 3E and 3G show 100× magnification; FIGS. 3B, 3D, 3F, and 3H show 400× magnification.

FIG. 4A is a graph of TNFα levels following treatment with ODN. BALB/c spleen cells were stimulated in vitro for 72 hours with 1 µM of various ODN. FIG. 4B is a graph of percent tumor necrosis factor alpha (TNFα) production versus suppressive ODN concentration. RAW 264.7 cells (106/well) were stimulated with 1 µM CpG plus increasing amounts of suppressive ODN. The concentration of TNF in culture supernatants after 24 hours was measured by ELISA. Data represent the mean±SEM of 5 independently studied animals/group. Statistical significance was assessed by Wilcoxon Rank sum test. FIG. 4C is a digital image of an agarose gel. Joints injected with 25 µg of ODN were processed into RNA 3 days later. Representative examples of local TNF and β-actin mRNA levels are shown. FIG. 4D is a graph of relative TNFα mRNA expression following treatment with CpG ODN or CpG ODN and suppressive ODN. Relative intensity of TNFα vs β-actin mRNA (N=3). The asterisk indicates that $p<0.05$.

FIGS. 10A through 10F are graphs showing the factors contributing to the suppression of CpG-induced immune activation. FIG. 10A is a graph showing that mammalian DNA suppresses CpG DNA-induced immune activation. FIG. 10B is a graph showing that the telomeric TTAGGG repetitive motif is suppressive. SEQ ID NOs: 2, 3, 4, 113 and 114 are shown. FIG. 10C is a graph showing that the suppressive motif is active in trans and cis conformations. FIG. 10D is a graph showing that suppressive ODNs selectively block CpG DNA-induced immune activation. FIG. 10E is a graph showing that Poly Gs are critical for suppression (SEQ ID NOs: 114-122 are shown). FIG. 10F is a graph showing that G-tetrad forming non-telomere sequences are also suppressive (SEQ ID NOs: 12 and SEQ ID NOs: 123-126 are shown).

FIG. 11A is a graph showing that oligonucleotides (ODNs) containing suppressive motifs inhibit CpG-induced immune activation in a dose dependent fashion. FIG. 11B is a graph showing G-tetrad formation and suppressive activity of phosphorothioate and 7-deaza guanosine (DG) modified ODNs.

BRIEF DESCRIPTION OF THE SEQUENCE LISTING

Figure 1:
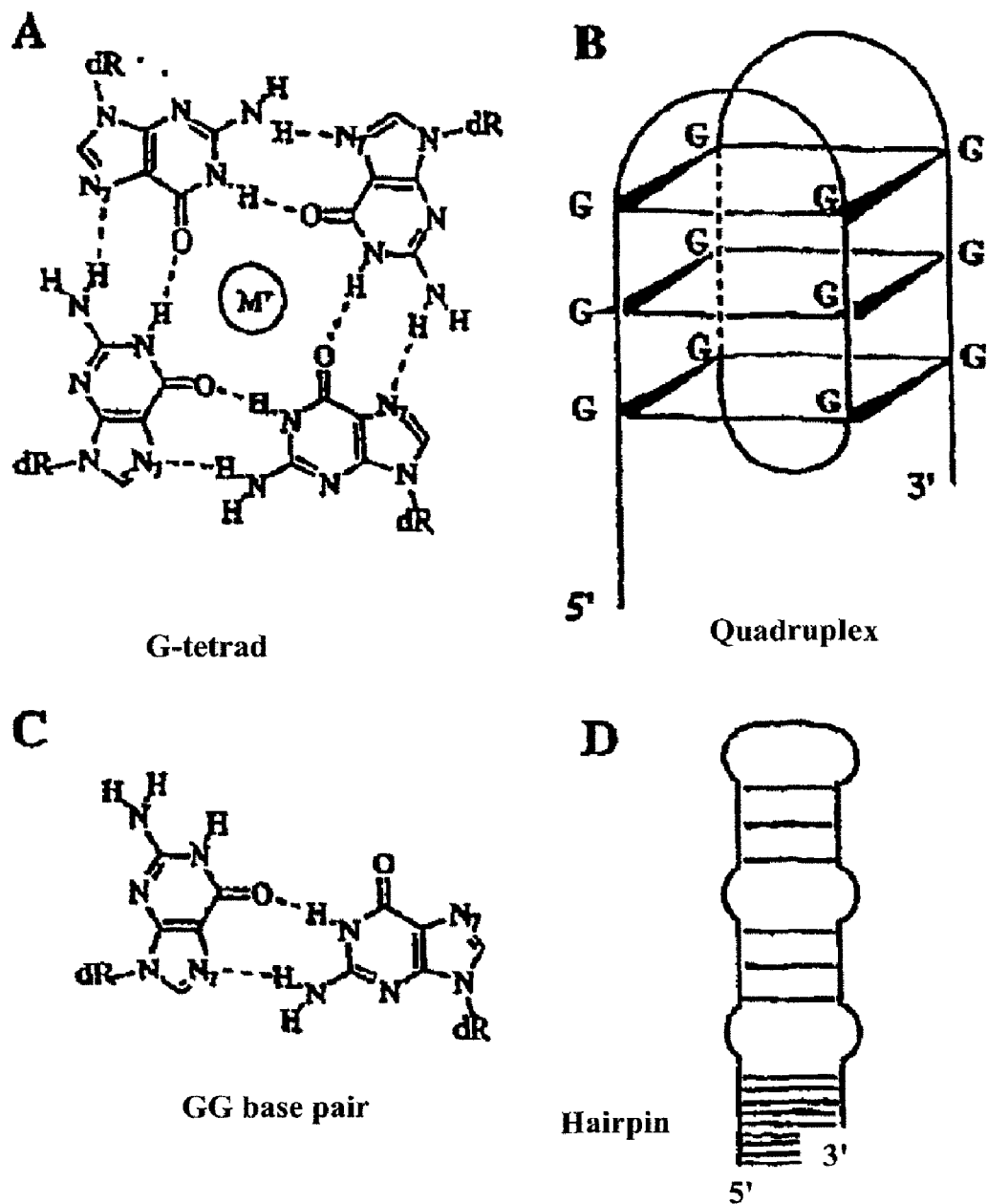
FIG. 1 is a set of diagrams of the structure of a G-tetrad.

SEQ ID NOs 1-25 are suppressive ODN sequences.
SEQ ID NOs 28, 29, and 31 are control ODN sequences.
SEQ ID NOs 26, 27, and 30 are immunostimulatory CpG sequences.
SEQ ID NOs 32-33 are TNFα primers.
SEQ ID NOs 34-35 are β-actin primers.
SEQ ID NOs 36-126 are ODN sequences.
The Sequence Listing is submitted as an ASCII text file [4239-66339-05_Sequence_Listing.txt, Apr. 22, 2011, 36.9 KB], which is incorporated by reference herein.

DETAILED DESCRIPTION OF SEVERAL EMBODIMENTS

I. Abbreviations
A: adenine
Ab: antibody
C: cytosine
CD: circular dichroism
CII: type II collagen
CII/CFA: type II collagen in complete Freund's adjuvant
CII/IFA: type II collagen in incomplete Freund's adjuvant
CpG ODN: an oligodeoxynucleotide including a CpG motif.
DC: dendritic cell
DG: deaza guanosine
ELISA: Enzyme-Linked Immunosorbent Assay
FCS: fetal calf serum
G: guanine
GI: gastrointestinal
GU: genitourinary
h: hour
IFN-α: interferon alpha
IFN-γ: interferon gamma
IL-10: interleukin 10
LPS: lipopolysaccharide
μg: microgram
mm: millimeter
mRNA: messenger ribonucleic acid
ODN: oligodeoxynucleotide
PBS: phosphate buffered saline
Pu: purine
Py: pyrimidine
s.c.: subcutaneous
SD: standard deviation
SE: standard error
T: thymine II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

5' and 3': DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

Animal: Living multi-cellular vertebrate organisms, a category that includes, for example, mammals and birds. The term mammal includes both human and non-human mammals. Similarly, the term "subject" includes both human and veterinary subjects.

Anti-inflammatory or anti-arthritis agent: A medication that, as well as having pain-relieving (analgesic) effects, has the effect of reducing inflammation when used over a period of time. Anti-inflammatory or anti-arthritis agents include both steroids and non-steroidal anti-inflammatory agents. Anti-inflammatory or anti-arthritis agents include, but are not limited to cortisone, prednisone, celecoxib, choline magnesium trisalicylate, diclofenac, diclofenac potassium, diclofenac XR, diflunisal, etodolac, etodolac ER, fenoprofen, flurbiprofen oral, ibuprofen, indomethacin, indomethacin SR, indomethacin suppositories, ketoprofen, ketoprofen ER, meclofenamate, meloxicam, nabumetone, naproxen, naproxen CR, naproxen ER, oxaprozin, piroxicam, rofecoxib, salsalate, sulindac, and tolmetin sodium.

Antigen: A compound, composition, or substance that can stimulate an immune response such as the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Antisense, Sense, and Antigene: Double-stranded DNA (dsDNA) has two strands, a 5'–>3' strand, referred to as the plus strand, and a 3'–>5' strand (the reverse compliment), referred to as the minus strand. Because RNA polymerase adds nucleic acids in a 5'–>3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target. In one embodiment, an antisense molecule specifically hybridizes to a target mRNA and inhibits transcription of the target mRNA.

Arthritis: Arthritis is an inflammatory disease that affects the synovial membranes of one or more joints in the body. It is the most common type of joint disease, and it is characterized by the inflammation of the joint. The disease is usually oligoarticular (affects few joints), but may be generalized. The joints commonly involved include the hips, knees, lower lumbar and cervical vertebrae, proximal and distal interphangeal joints of the fingers, first carpometacarpal joints, and first tarsometatarsal joints of the feet.

One type of arthritis is reactive arthritis, which is an acute nonpurulent arthritis secondary to a urinary tract or gastrointestinal infection with a variety of microorganisms, including *Chlamydia trachomatis, Yersinia, Salmonella, Shigella*, and *Campylobacter*. Microbial components are found in the affected joints. The arthritis appears abruptly and tends to involve the knees and ankles, but sometimes involves the wrists, fingers, and/or toes. Untreated, the arthritis lasts for about a year, then generally abates and only rarely is accompanied by ankylosing spondylitis. Despite evidence of disease being triggered by bacterial infection, viable bacteria are rarely present in affected joints and antibiotic treatment seldom provides relief.

Another type of arthritis is rheumatoid arthritis. Rheumatoid arthritis is a chronic, systemic, inflammatory disease that affects the synovial membranes of multiple joints in the body. Because the disease is systemic, there are many extra-articular features of the disease as well. For example, neuropathy, scleritis, lymphadenopathy, pericarditis, splenomegaly, arteritis, and rheumatoid nodules are frequent components of the disease. In most cases of rheumatoid arthritis, the subject has remissions and exacerbations of the symptoms. Rheumatoid arthritis considered an autoimmune disease that is acquired and in which genetic factors appear to play a role.

Autoimmune disorder: A disorder in which the immune system produces an immune response (for example, a B cell or a T cell response) against an endogenous antigen, with consequent injury to tissues. For example, rheumatoid arthritis is an autoimmune disorder, as are Hashimoto's thyroiditis, pernicious anemia, Addison's disease, type I diabetes, systemic lupus erythematosus, dermatomyositis, Sjogren's syndrome, dermatomyositis, lupus erythematosus, multiple sclerosis, myasthenia gravis, Reiter's syndrome, and Grave's disease, among others.

CD value: The formation of G-tetrads yields a complex with different physical properties than the individual oligonucleotides. Spectroscopically, this is manifested by an increase in circular dicroism (CD), and an increase in peak absorbance to the 260-280 nm wavelength owing to the formation of secondary structures. Thus, a convenient method for identifying oligonucleotides that form G-tetrads is to study their CD values. An increase in peak ellipticity values to greater than 2.0 is typical of a G-tetrad forming oligonucleotide. The higher the ellipticity value, the greater the tetrad-forming capacity of the oligonucleotide.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer part of the activity to the CpG oligodeoxynucleotide. A CpG oligonucleotide is an oligonucleotide that is at least about ten nucleotides in length and includes an unmethylated CpG. CpG oligonucleotides include both D and K type oligodeoxynucleotides (see below). CpG oligodeoxynucleotides are single-stranded. The entire CpG oligodeoxynucleotide can be unmethylated or portions may be unmethylated. In one embodiment, at least the C of the 5' CpG 3' is unmethylated.

Cytokine: Proteins made by cells that affect the behavior of other cells, such as lymphocytes. In one embodiment, a cytokine is a chemokine, a molecule that affects cellular trafficking.

D Type Oligodeoxynucleotide (D ODN): An oligodeoxynucleotide including an unmethylated CpG motif that has a sequence represented by the formula:

$$5' \text{ RY-CpG-RY } 3' \quad (SEQ \text{ ID NO: } 36)$$

wherein the central CpG motif is unmethylated, R is A or G (a purine), and Y is C or T (a pyrimidine). D-type oligodeoxynucleotides include an unmethylated CpG dinucleotide. Inversion, replacement or methylation of the CpG reduces or abrogates the activity of the D oligodeoxynucleotide.

In one embodiment, a D type ODN is at least about 16 nucleotides in length and includes a sequence represented by Formula III of PCT Application No. PCT/US02/30532, which is incorporated by reference herein. The oligonucleotides have a sequence set forth as:

$$\text{(SEQ ID NO: 36-112)}$$
$$5' \ X_1X_2X_3 \ Pu_1 \ Py_2 \ CpG \ Pu_3 \ Py_4 \ X_4X_5X_6(W)_m(G)_N\text{-}3'$$

wherein the central CpG motif is unmethylated, Pu is a purine nucleotide, Py is a pyrimidine nucleotide, X and W are any nucleotide, M is any integer from 0 to 10, and N is any integer from 4 to 10. Generally D ODNs can stimulate a cellular response. For example, D ODNs stimulate natural killer cells and the maturation of dendritic cells.

Epitope: An antigenic determinant. These are particular chemical groups or peptide sequences on a molecule that are antigenic, for example, that elicit a specific immune response. An antibody binds a particular antigenic epitope.

Functionally Equivalent: Sequence alterations, for example in a suppressive ODN, that yield the same results as described herein. Such sequence alterations can include, but are not limited to, deletions, base modifications, mutations, labeling, and insertions.

G-tetrad: G-tetrads are G-rich DNA segments that can accommodate complex secondary and/or tertiary structures (see FIG. 1). A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of contiguous Gs, and the higher the G content of the ODN, the higher the likelihood of G-tetrad formation, as reflected by higher CD or ellipticity values.

Oligonucleotides that form G-tetrads can also form higher-level aggregates that are more easily recognized and taken up by immune cells, for example, through scavenger receptors or by nucleolin.

Guanosine-rich sequence: A hexameric region of a nucleotide sequence in which >50% of the bases are Gs.

Immediately adjacent: Two nucleic acid sequences are "immediately adjacent" if a spacer of 0-9 nucleotides is included between the nucleic acid sequences. In one example, one nucleic acid sequence includes an immunostimulatory CpG motif and the other nucleic acid sequence is a suppressive nucleic acid sequence. Thus an immunostimulatory CpG motif and the suppressive ODN sequence are immediately adjacent if they are separated by less than 9 nucleotides.

Immunostimulatory CpG ODN: An oligodeoxynucleotide, which contains a cytosine, guanine dinucleotide sequence and stimulates (for example, has a mitogenic effect) vertebrate immune cells. The cytosine, guanine is unmethylated. Both D and K type CpG ODNs are immunostimulatory (see in Verthelyi et al., *J. Immunol.* 166:2372-2377, 2001, which is herein incorporated by reference).

Immunosuppressive agent: A molecule, such as a chemical compound, small molecule, steroid, nucleic acid molecule, or other biological agent, that can decrease an immune response such as an inflammatory reaction. Immunosuppressive agents include, but are not limited to an agent of use in treating arthritis (anti-arthritis agent). Specific, non-limiting examples of immunosuppressive agents are non-steroidal anti-inflammatory agents, cyclosporine A, FK506, and anti-CD4. In additional examples, the agent is a biological response modifier, such as KINERET® (anakinra), ENBREL® (etanercept), or REMICADE® (infliximab), a disease-modifying antirheumatic drug (DMARD), such as ARAVA® (leflunomide), a nonsteroidal anti-inflammatory drug (NSAID), specifically a Cyclo-Oxygenase-2 (COX-2) inhibitor, such as CELEBREX® (celecoxib) and VIOXX® (rofecoxib), or another product, such as HYALGAN® (hyaluronan) and SYNVISC® (hylan G-F20).

Immune response: A response of a cell of the immune system, such as a B cell or T cell to a stimulus. In one embodiment, the response is specific for a particular antigen (an "antigen-specific response").

Infectious agent: An agent that can infect a subject, including, but not limited to, viruses, bacteria, and fungi.

Examples of infectious virus include: Retroviridae (for example, human immunodeficiency viruses, such as HIV-1 (also referred to as HTLV-III, LAV or HTLV-III/LAV, or HIV-III; and other isolates, such as HIV-LP; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (for example, reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxyiridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (for example, Hepatitis C); Norwalk and related viruses, and astroviruses).

Examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli.*

Examples of infectious fungi include, but are not limited to, *Cryptococcus neoformans, Histoplasma capsulatum, Coccidioides immitis, Blastomyces dermatitidis, Chlamydia trachomatis*, and *Candida albicans.*

Other infectious organisms (such as protists) include: *Plasmodium falciparum* and *Toxoplasma gondii.*

Inflammatory arthropathy: An inflammatory arthropathy is an inflammatory disease affecting one or more joints, such as an inflammatory disease that affects the synovial membranes of one or more joints. Inflammatory arthropathies include, for example, arthritis, ankylosing spondylitis, Reiter's syndrome, psoriatic arthropathy, enteropathis spondylitis, juvenile arthropathy, and reactive arthropathy.

Isolated: An "isolated" biological component (such as a nucleic acid, peptide or protein) has been substantially separated, produced apart from, or purified away from other biological components in the cell of the organism in which the component naturally occurs, for example, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

K Type Oligodeoxynucleotide (K ODN): An oligodeoxynucleotide including an unmethylated CpG motif that has a sequence represented by the formula:

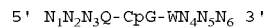

$$5'\ N_1N_2N_3Q\text{-}CpG\text{-}WN_4N_5N_6\ 3'$$

wherein the central CpG motif is unmethylated, Q is T, G or A, W is A or T, and $N_1$, $N_2$, $N_3$, $N_4$, $N_5$, and $N_6$ are any nucleotides. In one embodiment, Q is a T. Generally K ODNs can stimulate a humoral response. For example, K ODNs stimulate the production of IgM. K type CpG ODNs have been previously described (see U.S. Pat. Nos. 6,194,388; 6,207,646; 6,214,806; 6,218,371; 6,239,116; 6,339,068; 6,406,705, and 6,429,199, which are herein incorporated by reference).

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphonuclear leukocytes (neutrophils, eosinophils, basophils) and mononuclear leukocytes (monocytes and lymphocytes). When an infection is present, the production of leukocytes increases.

Maturation: The process in which an immature cell, such as dendritic cell, changes in form or function to become a functional mature cell, such as an antigen presenting cell (APC).

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or oligo: Multiple nucleotides (for example, molecules comprising a sugar, for example, ribose or deoxyribose) linked to a phosphate group and to an exchangeable organic base, which is either a substituted pyrimidine (Py) (for example, cytosine (C), thymine (T) or uracil (U)) or a substituted purine (Pu) (for example, adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (an oligonucleotide minus the phosphate) and any other organic base polymer. Oligonucleotides can be obtained from existing nucleic acid sources (for example, genomic or cDNA), but are preferably synthetic (for example, produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," or "CpG ODN," refers to an oligodeoxynucleotide, which contains a cytosine, guanine dinucleotide sequence and stimulates (for example, has a mitogenic effect) vertebrate immune cells. The cytosine, guanine is unmethylated.

An "oligonucleotide delivery complex" is an oligonucleotide associated with (for example, ionically or covalently bound to; or encapsulated within) a targeting means (for example, a molecule that results in a higher affinity binding to a target cell (for example, B-cell or natural killer (NK) cell) surface and/or increased cellular uptake by target cells). Examples of oligonucleotide delivery complexes include oligonucleotides associated with: a sterol (for example, cholesterol), a lipid (for example, cationic lipid, virosome or liposome), or a target cell specific binding agent (for example, a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167: 3324, 2001)

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, intra-articularly, or subcutaneously, and various surface applications including intranasal, intradermal, and topical application.

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to a disease such as an autoimmune disorder. An example of a person with a known predisposition is someone with a history of diabetes in the family, or who has been exposed to factors that predispose the subject to a condition, such as lupus or arthritis. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Suppressive ODN: DNA molecules of at least eight nucleotides in length, wherein the oligodeoxynucleotide forms a G-tetrad, and has a CD value of greater than about 2.9. In a suppressive ODN the number of guanosines is at least two. In one embodiment, a suppressive ODN inhibits immune activation caused by CpG DNA when administered prior to, concurrently with, or after the administration of a CpG ODN at least about 8 nucleotides in length.

Therapeutic agent: Used in a generic sense, it includes treating agents, prophylactic agents, and replacement agents.

Therapeutically effective amount of [a compound]: A quantity of a specified compound sufficient to achieve a desired effect in a subject being treated. For instance, this can be the amount of a suppressive ODN necessary to suppress CpG-induced immune cell activation in a subject, or a dose sufficient to prevent advancement, or to cause regression of a disease, or which is capable of relieving symptoms caused by a disease, such as pain or swelling.

The therapeutically effective amount of a suppressive ODN can be administered systemically or locally. In addition, a therapeutically effective amount of a suppressive ODN can be administered in a single dose, or in several doses, for example daily, during a course of treatment. However, the therapeutically effective amount of the ODN will be dependent on the preparation applied, the subject being treated, the severity and type of the affliction, and the manner of administration of the compound. For example, a therapeutically effective amount of a suppressive ODN can vary from about 0.01 mg/kg body weight to about 1 g/kg body weight in some embodiments, or from about 0.01 mg/kg to about 60 mg/kg of body weight, based on efficacy.

Therapeutically effective dose: A dose sufficient to prevent advancement, or to cause regression of the disease, or which is capable of relieving symptoms caused by the disease, such as pain or swelling.

III. Description of Several Embodiments

A. Suppressive Oligodeoxynucleotides and Guanosine-Quadruplexes (G-Tetrads)

The present disclosure relates to a class of DNA motifs that selectively inhibits or suppresses immune activation. Optimal activity is observed using multimers of these motifs, which are rich in G bases and capable of forming G-quadruplexes (G-tetrads). G-tetrads are G-rich DNA segments that can accommodate complex secondary and/or tertiary structures (see FIG. 1). The suppressive ODNs of the disclosure are highly specific (for example, are neither toxic nor non-specifically immunosuppressive), and are useful for inhibiting an immune response. In one embodiment, a suppressive ODN is of use for blocking an immune response, such as an autoimmune response.

A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of continuous Gs, and the higher the G content of the ODN, the higher the likelihood of G-tetrad formation, as reflected by higher ellipticity values.

Oligonucleotides that form G-tetrads can also form higher-level aggregates that are more easily recognized and taken up by immune cells, for example, through scavenger receptors or by nucleolin.

The formation of G-tetrads yields a complex with different physical properties than the individual oligonucleotides. Spectroscopically, this is manifested by an increase in circular dicroism (CD), and an increase in peak absorbance to the 260-280 nm wavelength owing to the formation of secondary structures. Thus, a convenient method for identifying oligonucleotides that form G-tetrads is to study their CD values. An increase in peak ellipticity values to greater than 2.0 is typical of a G-tetrad forming oligonucleotide. For instance, G-tetrad-forming ODNs can have CD values of about 2.2, 2.4, 2.6, 2.8, 3.0, 3.2, 3.5, 4.0, 4.5, 5.0, 5.5, 6.0, 6.5, 7.0, 7.5, 8.0, 8.5, 9.0, or higher. The higher the ellipticity value, the greater the tetrad-forming capacity of the oligonucleotide, so an ODN with a CD value of about 8.5 is typically more suppressive than an ODN with a CD value of about 2.9.

In some embodiments, the ODN is from about 8 to about 100 nucleotides in length. In particular examples, the ODN is from about 10 to about 30 nucleotides in length. Optionally, the suppressive ODN has multiple guanosine-rich sequences, for example, in certain embodiments the ODN has from about two to about 20 guanosine-rich sequences, or, more particularly, from about two to about four guanosine-rich sequences.

In one embodiment, the suppressive ODNs have a sequence comprising at least one of the human telomere-derived TTAGGG suppressive motifs (see Example 1). In some examples, the ODN has at least one TTAGGG motif, and in certain examples, the ODN has multiple TTAGGG motifs. For example, in particular examples, the ODN has from about two to about 20 TTAGGG motifs, or from about two to about four TTAGGG motifs. In this embodiment, suppressive ODNs containing multiple TTAGGG repeats are the most suppressive. Single TTAGGG motifs are suppressive only when incorporated into larger ODNs with greater than 10 bases.

Suppression of CpG-induced immune activation requires a G-tetrad-forming sequence that imposes the two-dimensional structure necessary for G-tetrad formation. Examples of suppressive ODN include, but are not limited to, those shown in FIG. 9. However, any oligonucleotide capable of forming G-tetrads may be used to suppress CpG DNA-induced immune activation. In particular examples, the ODN includes selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

Furthermore, in particular embodiments the ODN is modified to prevent degradation and increase stability. In one embodiment, suppressive ODNs can include modified nucleotides to confer resistance to degradation. Thus, because phosphorothioate-modified nucleotides confer resistance to exonuclease digestion, a suppressive ODN can be "stabilized" by incorporating phosphorothioate-modified nucleotides.

In some embodiments, the ODN has a phosphate backbone modification, and in particular examples, the phosphate backbone modification is a phosphorothioate backbone modification. In one embodiment, the guanosine-rich sequence and its immediate flanking regions include phosphodiester rather than phosphorothioate nucleotides. In one specific non-limiting example, the sequence TTAGGG includes phosphodiester bases. In some examples, all of the bases in an ODN are phosphodiester bases. In other examples, the ODN is a phosphorothioate/phosphodiester chimera.

As disclosed herein, any suitable modification can be used to render the ODN resistant to degradation in vivo (for example, via an exo- or endo-nuclease). In one specific, non-limiting example, a modification that renders the ODN less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (for example, those in which the charged phosphonate oxygen is replaced with an alkyl or aryl group, as set forth in U.S. Pat. No. 4,469,863), phosphodiesters and alkylphosphotriesters (for example, those in which the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

The suppressive ODN of the disclosure can be synthesized by standard methods well known in the art. Most commonly, synthesis is performed on an oligonucleotide synthesizer using the standard cyanoethyl phosphoramidite chemistry. These include, but are not limited to, phosphodiester, phosphorothioate, peptide nucleic acids, synthetic peptide analogues, and any combination thereof. Those skilled in the art will recognize that any other standard technique may be used to synthesize the suppressive ODN described herein.

The suppressive ODN can be included in a single polynucleotide that also includes an immunostimulatory CpG motif, such as a D or a K type oligonucleotide sequence. Generally, if a suppressive ODN sequence and an immunostimulatory ODN sequence are included in the a single polynucleotide, the polynucleotide selectively inhibits or suppresses immune activation.

In one example, a polynucleotide that selectively inhibits or suppresses immune activation includes an immunostimulatory CpG motif placed 5' to a suppressive ODN sequence. In this embodiment, a spacer of at least 10 nucleotides is included between the CpG motif and the suppressive ODN sequence in the polynucleotide. The spacer can be any nucleotide sequence of interest, provided it does not include an immunostimulatory CpG motif or the sequence of a suppressive ODN. In one embodiment, the single polynucleotide includes an immunostimulatory CpG motif placed 5' to a suppressive ODN sequence, wherein the immunostimulatory CpG motif is separated from the suppressive ODN sequence by at least 10 nucleotides. Thus, in several examples, the immunostimulatory CpG motif is separated from the suppressive ODN sequence by at least about 10, about 15, about 20, about 25, about 50 or about 100 nucleotides in a single polynucleotide. Spacers of about at least about 100 nucleotides, at least about 500 nucleotides, or at least about a kilobase can also be utilized.

A polynucleotide that selectively inhibits or suppresses immune activation does not include an immunostimulatory CpG motif placed immediately adjacent (5') to a suppressive ODN sequence. Thus, a polynucleotide that selectively inhibits or suppresses immune activation does not include a 5' immunostimulatory CpG motif separated by less than 9 bases from a 3' suppressive ODN sequence.

In another example, a polynucleotide that selectively inhibits or suppresses immune activation includes an immunostimulatory CpG motif placed 3' to a suppressive ODN sequence. The immunostimulatory CpG motif can be placed immediately adjacent (3') to a suppressive ODN. In one example, a polynucleotide that selectively inhibits or suppresses immune activation can include a 3' immunostimulatory CpG motif separated by less than 9 bases from a 5' suppressive ODN. In another example, a spacer of any length can be included between the 3' immunostimulatory CpG motif and the 3' suppressive ODN. In a further example, a spacer of at least one, at least two, at least ten, at least 100, or several kilobases can be inserted between the 3' immunostimulatory CpG motif and the suppressive ODN. Thus, any oligonucleotide including an immunostimulatory CpG motif positioned 3' of a suppressive ODN sequence selectively inhibits or suppresses immune activation. In addition, any double stranded nucleic acid that includes a suppressive ODN sequence and immunostimulatory CpG motif in trans (on opposite strands of the double stranded nucleic acid) selectively inhibits or suppresses immune activation.

In one embodiment, a suppressive ODN is included in a delivery complex.

The delivery complex can include the suppressive ODN and a targeting means. Any suitable targeting means can be used. For example, in some embodiments, a suppressive ODN is associated with (for example, ionically or covalently bound to, or encapsulated within) a targeting means (for example, a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). Examples of oligodeoxynucleotide delivery complexes include a suppressive ODN associated with a sterol (for example, cholesterol), a lipid (for example, a cationic lipid, anionic lipid, virosome or liposome), and a target cell specific binding agent (for example, a ligand recognized by target cell specific receptor). Without being bound by theory, the complex is sufficiently stable in vivo to prevent significant uncoupling prior to delivery to the target cell. In one embodiment, the delivery complex is cleavable such that the ODN is released in a functional form at the target cells.

B. Pharmaceutical Compositions

The suppressive ODNs described herein may be formulated in a variety of ways depending on the location and type of disease to be treated. Pharmaceutical compositions are thus provided for both local (for example, intra-articluar) use as well as for systemic use. Therefore, the disclosure includes within its scope pharmaceutical compositions comprising at least one suppressive ODN formulated for use in human or veterinary medicine.

Pharmaceutical compositions that include at least one suppressive ODN as described herein as an active ingredient, or that includes both a suppressive ODN and additional agents, such as anti-inflammatory or anti-arthritis factors as active ingredients, can be formulated with an appropriate solid or liquid carrier, depending upon the particular mode of administration chosen. Additional active ingredients include, for example, biological response modifiers, such as KINERET® (anakinra), ENBREL® (etanercept), or REMICADE® (infliximab), disease-modifying antirheumatic drugs (DMARDs), such as ARAVA® (leflunomide), steroids, such as prednisone or cortisone, nonsteroidal anti-inflammatory drugs (NSAIDs), such as celecoxib, choline magnesium trisalicylate, diclofenac, diclofenac potassium, diclofenac XR, diflunisal, etodolac, etodolac ER, fenoprofen, flurbiprofen oral, ibuprofen, indomethacin, indomethacin SR, indomethacin suppositories, ketoprofen, ketoprofen ER, meclofenamate, meloxicam, nabumetone, naproxen, naproxen CR, naproxen ER, oxaprozin, piroxicam, rofecoxib, salsalate, sulindac, or tolmetin sodium, or other products, such as HYALGAN® (hyaluronan) and SYNVISC® (hylan G-F20).

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutical compositions that comprise a suppressive ODN, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

C. Therapeutic Uses

A method is disclosed herein for treating or preventing an inflammatory arthropathy in a subject. Inflammatory arthropathies include, but are not limited to reactive arthritis and rhematoid arthritis. The method includes administering a therapeutically effective amount of the suppressive ODN to a subject having or at risk of developing inflammatory arthropathy, thereby treating or preventing the inflammatory arthropathy. In one embodiment, the suppressive ODN can be administered locally, such as by intra-articular injection. In another embodiment, the suppressive ODN is administered systemically.

In order to treat or prevent an inflammatory arthropathy, a therapeutically effective amount of a suppressive ODN (see above) is administered to the subject. In one embodiment, the ODN has a CD value of greater than about 2.9, 3.0, 3.2, 3.4, 3.6, 3.8, 4.0, or 5.0. In some embodiments of the method, the ODN is from about 8 to about 100 nucleotides in length. In particular examples of the method, the ODN is from about 10 to about 30 nucleotides in length. Optionally, the suppressive ODN has multiple guanosine-rich sequences, for example, in certain embodiments of the method, the ODN has from about two to about 20 guanosine-rich sequences, or, more particularly, from about two to about four guanosine-rich sequences.

In some examples of the method, the ODN has at least one TTAGGG motif, and in certain examples, the ODN has multiple TTAGGG motifs. For example, in particular examples of the method, the ODN has from about two to about 20

TTAGGG motifs, or from about two to about four TTAGGG motifs. In particular examples of the method, the ODN has a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

Combinations of these suppressive ODN are also of use. Thus, in one embodiment, more than one suppressive ODN, each with a different nucleic acids sequence, are administered to the subject. In several specific, non-limiting examples, at least two, at least three, or at least four suppressive ODN are administered to the subject.

In another embodiment an additional anti-inflammatory agent is administered in conjunction with a suppressive ODN. The agent can be an immunosuppressive, or an anti-arthritis agent. The administration of the anti-arthritis agent and the suppressive ODN can be sequential or simultaneous.

In particular examples, the anti-arthritis agent is a biological response modifier, such as KINERET® (anakinra), ENBREL® (etanercept), or REMICADE® (infliximab), a disease-modifying antirheumatic drug (DMARD), such as ARAVA® (leflunomide), a steroid, such as prednisone or cortisone, a nonsteroidal anti-inflammatory drug (NSAID), such as celecoxib, choline magnesium trisalicylate, diclofenac, diclofenac potassium, diclofenac XR, diflunisal, etodolac, etodolac ER, fenoprofen, flurbiprofen oral, ibuprofen, indomethacin, indomethacin SR, indomethacin suppositories, ketoprofen, ketoprofen ER, meclofenamate, meloxicam, nabumetone, naproxen, naproxen CR, naproxen ER, oxaprozin, piroxicam, rofecoxib, salsalate, sulindac, or tolmetin sodium, or another product, such as HYALGAN® (hyaluronan) or SYNVISC® (hylan G-F20).

Thus, the suppressive ODNs disclosed herein may be administered to a subject for the treatment of inflammatory arthropathies in that individual. ODN administration can be systemic or local. Local administration of the ODN is performed by methods well known to those skilled in the art. By way of example, one method of administration to the knee, hip and/or shoulder of an individual is by intra-articular injection. For administration to the knee, for example, the joint to be injected is washed with a betadine solution or other antiseptic. A solution of an anesthetic, such as about one percent lidocaine hydrochloride is injected into the skin and subcutaneous tissue. A 3-way stopcock/needle assembly is utilized to administer the compound via an 18-30 gauge needle. The ODN is injected into the joint space using a standard lateral approach well known to those skilled in the art. The needle and needle tract are cleansed by flushing with 1% lidocaine hydrochloride through the 3-way stopcock assembly as the needle is withdrawn. The knee is then moved through a flexion-extension arc and then immobilized in full extension. The patient is then confined to bed for approximately 24 hours to minimize movement and minimize leakage of ODN from the joint.

In other embodiment, the administration of the suppressive ODN is systemic. Oral, intravenous, intra-arterial, subcutaneous, intra-peritoneal, intra-muscular, and even rectal administration is contemplated.

Other embodiments are methods of treating or preventing inflammatory arthropathies in a subject that involves contacting immune cells with a suppressive ODN, and transferring the immune cells to a subject having or at risk of developing inflammatory arthropathies, thereby treating or preventing the inflammatory arthropathies. Without being bound by theory, these immune cells act to suppress immune activation in a subject. One specific, non-limiting example is dendritic cells. Thus, in certain examples, the immune cells, such as dendritic cells, are contacted with a suppressive ODN, and subsequently administered to a subject. The immune cells can be delivered alone, in conjunction with a suppressive ODN, and/or in conjunction with an additional immunosuppressive agent. The immune cells can be delivered either systemically or locally. In several specific, non-limiting examples, the cells are delivered parenterally, intravenously, intra-muscularly, sub-cutaneously, or intra-articularly.

Precise, effective quantities of cells can be readily determined by those who are skilled in the art and will depend, of course, upon the exact condition being treated by the particular therapy being employed. The cells can be transplanted to a desired location, or can be administered intravenously. Other agents, such as growth factors or immunosuppressive agents, can be administered in conjunction with the immune cells.

D. Kits

Further embodiments of the disclosure include kits useful for administering the suppressive ODN described herein in vivo or in vitro. For example, a kit useful for treating a subject with inflammatory arthropathies would comprise an appropriate dosage of suppressive ODN, as well as, optionally, any agents useful for enhancing the inhibitory effect of suppressive ODN. Other embodiments further include instructions for using the kit, and/or pre-filled syringes for administering the ODN to a subject.

Thus, in one embodiment, a kit is provided including a container of suppressive ODN (a sufficient amount for either a single use or multiple uses), and instructions the suppressive ODN. The instructions can be in written form, or can be provided in an electronic format, such as on a diskette or a CD-ROM. Instructions can also be provided in the form of a video cassette.

The subject matter of the present disclosure is further illustrated by the following non-limiting Examples.

EXAMPLES

Example 1

Reduction of CpG-Induced Arthritis by Suppressive Oligodeoxynucleotides

This example demonstrates the influence of CpG DNA and suppressive ODNs on the propensity of the host to develop arthritis, and indicates that the mechanism of suppressive ODN action is mediated by Cd11c positive cells.

A. General Methods

Animals:

Female BALB/c mice were obtained from the Jackson Laboratories (Bar Harbor, Me.). The studies were conducted using 8-20 week old mice.

Oligodeoxynucleotides:

ODNs were synthetically produced. Sequences of the phosphorothioate ODN used were:

```
CpG:         GCTAGACGTTAGCGT    (SEQ ID NO: 30)
suppressive: CCTCAAGCTTGAGGGG   (SEQ ID NO: 1)
control:     GCTAGATGTTAGCGT.   (SEQ ID NO: 31)
```

All ODN were free of detectable protein or endotoxin contamination.

Experimental Protocol:

25 µg of ODN in 6 µl of PBS was injected into the knee joint using a 30 gauge needle. In some studies, knees were re-injected with PBS or 25 µg of suppressive ODN 24-48 hours after initial CpG ODN administration. Joint swelling was measured in the coronal plane using a micrometer caliper. Histologic analysis was performed by a blinded investigator on fixed, decalcified and paraffin embedded sections stained with hematoxylin/eosin.

TNFα Assays:

Single spleen cell suspensions were prepared in RPMI-1640 supplemented with 5% heat inactivated fetal calf serum, 1.5 mM L-glutamine and 100 U/ml of penicillin/streptomycin. $5 \times 10^5$ cells/well were cultured in flat-bottomed microtiter plates (Costar, Corning, N.Y.) with ODN for 72 hr. TNFα levels in culture supernatants were measured by ELISA. In brief, 96-well Immulon H2B plates were coated with anti-TNFα Ab (Genzyme, Cambridge, Mass.). Plates were blocked with PBS—1% BSA and overlaid with culture supernatants. Bound cytokine was detected by the addition of biotin labeled anti-TNFα Ab (Genzyme, Cambridge, Mass.) followed by phosphatase-conjugate avidin.

RT-PCR:

Total RNA was extracted from homogenized knees using TRIzol reagent (GibCO Life Technologies, Gaithersburg, Md.) as recommended by the manufacturer. 5 µg of total RNA was reverse transcribed into cDNA, which was assayed for TNFα (sense ATGAGCACAGAAAGCATGATC; SEQ ID NO:32, antisense TACAGGCTTGTCACTCGAATT; SEQ ID NO:33, 275 bp) and β-actin (sense GACATGGAG-GAGTCTGGCACCACA; SEQ ID NO:34, antisense ATCTCCTGCTCGAAGTCTAGAGCAA; SEQ ID NO:35, 440 bp) by PCR as previously described (Takeshita et al., *Neuroreport* (2001) 12:3029-3032). Relative band intensity was determined by ethidium bromide staining of 1% agarose gels using NIH-Image software.

Statistical Analysis:

Statistically significant differences between two groups were determined using the Wilcoxon Rank Sum Test. When comparing more than two groups, a two-tailed non-parametric ANOVA with Dunn's post-test analysis was used. Differences in joint diameters were analyzed by repeated-measures ANOVA using the Proc Mixed procedure from the Statistical Analysis System (SAS). A p value of <0.05 was considered significant.

B. Induction of Arthritis by CpG ODN

Microbial infection of the gastrointestinal (GI) or genitourinary (GU) tracts is associated with the development of reactive arthritis in humans. Evidence indicates that bacterial DNA contributes to this process, since 1) bacterial DNA can be detected in arthritic joints (Braun et al., *J. Rheumatol.* (2000) 27:2185-2192), and 2) bacterial DNA induces joint inflammation when injected into the knees of normal mice (Deng et al., *Nat. Med.* (1999) 5:702-705). Deng et al. established that immunostimulatory CpG motifs were the cause of this inflammation by showing that CpG-containing oligodeoxynucleotides (ODN) induced disease in a manner similar to that induced by purified bacterial DNA (Deng et al., supra). This effect is consistent with the proinflammatory properties of CpG ODN, including their ability to stimulate immune cells to proliferate, differentiate, and secrete proinflammatory chemokines and cytokines (Deng et al., supra; Klinman et al., *Springer Semin. Immunopathol.* (2000) 22:173-83).

Figure 2:
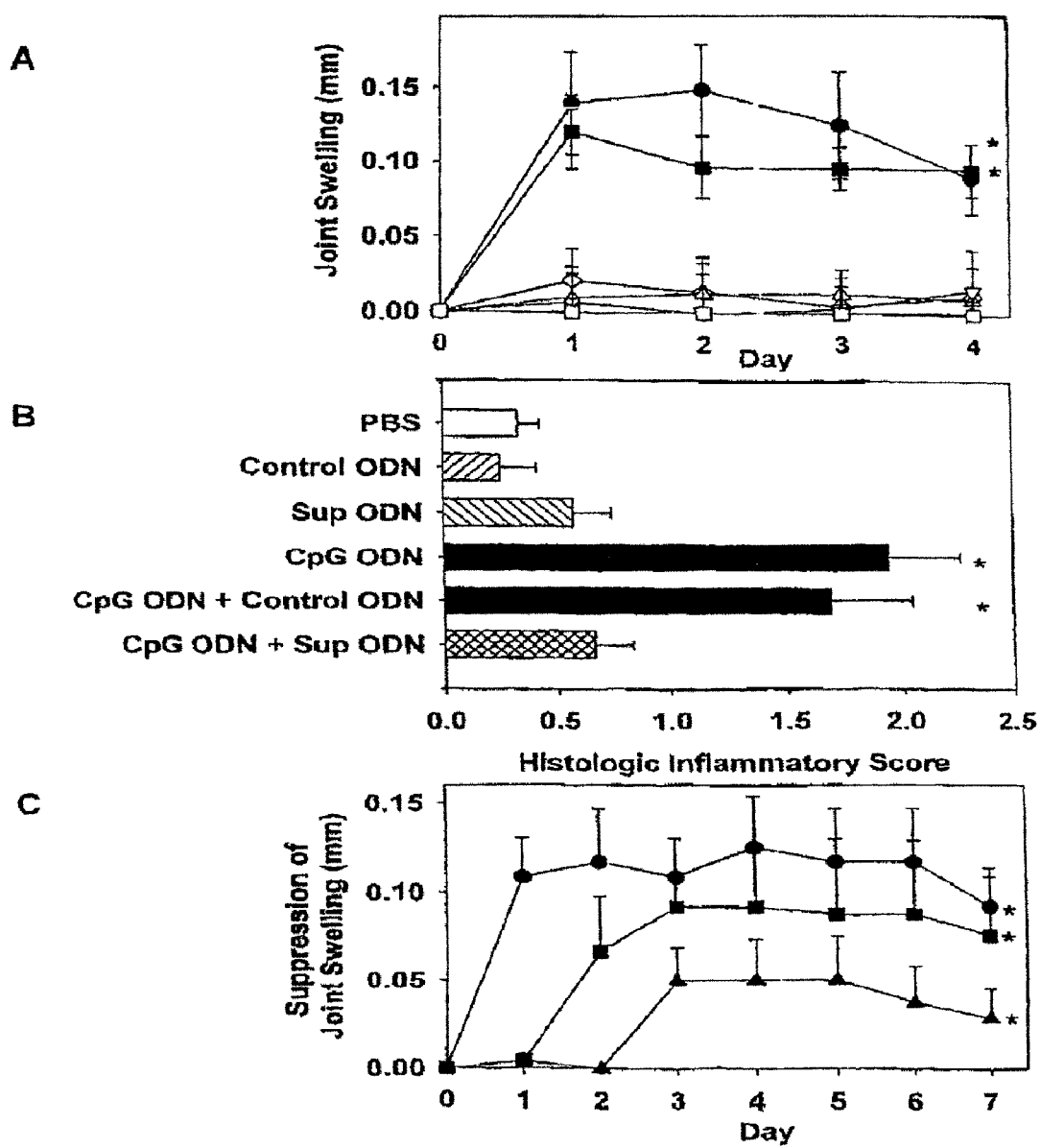
FIG. 2 is a set of graphs showing the effect of CpG ODN and suppressive ODN injection into the knee.

Consistent with the findings of Deng et al. (Deng et al., *Arthritis Rheum.* (2000) 43:356-364), BALB/c knees injected with CpG ODN developed inflammatory arthritis within 24 hr that peaked after 3-7 days (FIG. 2). CpG-induced arthritis was characterized by swelling (0.14+0.04 milimeters (mm) versus 0.02+0.02, p=0.054) and histological changes that included perivascular infiltration by mononuclear cells and hyperplasia of the synovial lining (FIG. 2). These inflammatory effects were CpG-specific and localized, since no disease was observed in contra-lateral knees injected with PBS or control ODN. Similar swelling and histologic changes were observed in knees injected with bacterial DNA.

C. Suppressive ODN Block the Development of CpG-Induced Arthritis

To determine whether suppressive ODN prevent CpG mediated inflammatory arthritis, knees were co-injected with 25 µg of suppressive plus 25 µg of CpG ODN. The inclusion of suppressive ODN reduced swelling from 0.14+0.04 mm to 0.02+0.02 mm (p=0.004) and the inflammatory score from 1.94+0.32 to 0.67+0.12 (p=0.018, FIG. 2). When joint inflammation was assessed by magnetic resonance imaging, suppressive ODN reduced CpG ODN induced fluid accumulation from 95.4+8.2 MR-signal intensity units to 52.3+6.7 units (n=5, p<0.001). These effects were specific, since co-administering PBS or control ODN had no impact on CpG-induced arthritis (FIG. 2). In parallel studies, suppressive ODN prevented the arthritis induced by bacterial DNA but not lipopolysaccharide (LPS).

D. Kinetics of the ODN Anti-Inflammatory Effect

To examine the kinetics of this anti-inflammatory effect, suppressive ODN were administered 0, 24 and 48 hours after CpG ODN injection. To control for the effect of multiple injections, the contralateral knee was injected with PBS, and the difference in swelling between the two joints evaluated daily. A significant reduction in swelling was observed when joints were treated with suppressive ODN up to two days after CpG administration (p=0.012, FIG. 2C). However, maximal control of arthritis required early intervention (p=0.011, D0 vs D2).

E. Suppressive ODNs Reduce Intra-Articular TNF Production

Figure 3:
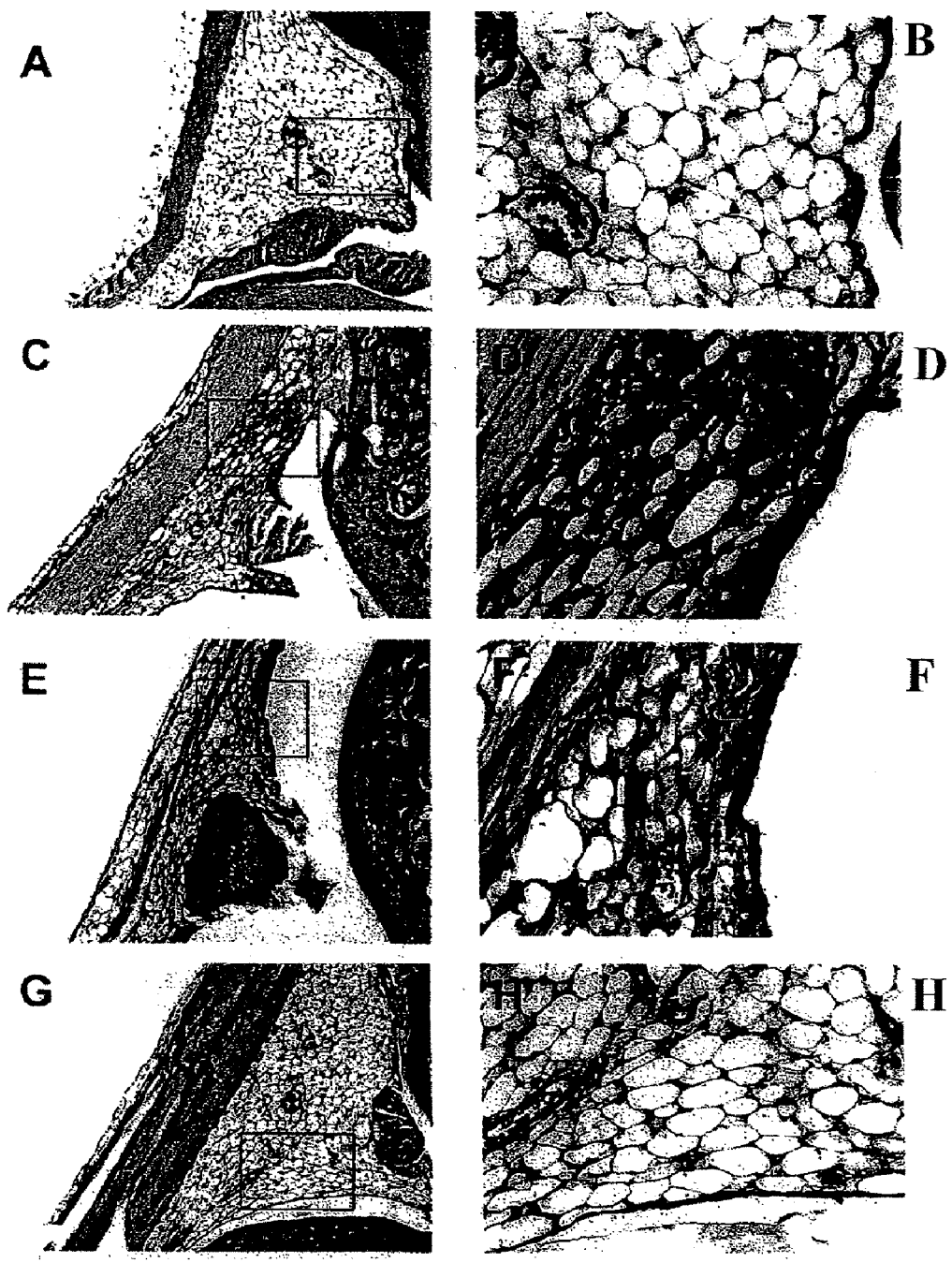
FIG. 3 is a set of digital images of a photomicrograph showing the effects of CpG and ODN injection on knee histology in mice. BALB/c knees were injected with PBS (FIG. 3A, B), CpG ODN (FIG. 3C, D), CpG plus control ODN (FIG. 3E, F) or CpG plus suppressive ODN (25 µg of each ODN, FIG. 3G, H). Typical histology four days after injection of 25 µg of each ODN is shown. Note the cellular infiltrates, perivascular accumulation of mononuclear cells, and hyperplasia of the synovial lining in the knees of mice injected with CpG ODN.
Figure 4:
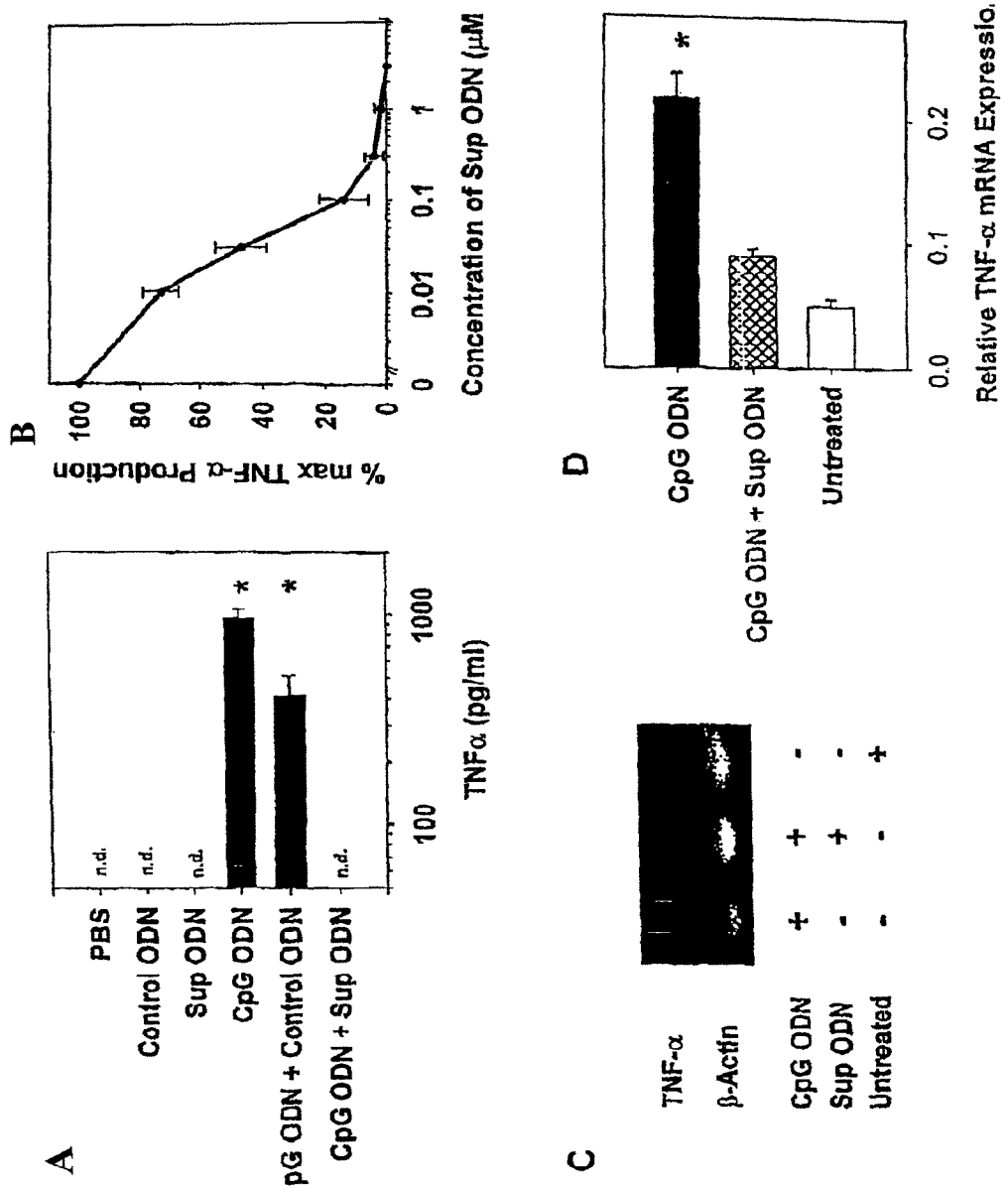
FIG. 4 is a set of graphs that demonstrate that administration of suppressive ODN decreases TNFα upregulation following CpG ODN injection.

Previous studies established that the magnitude of CpG-induced arthritis correlated with intra-articular TNFα levels (Deng et al., *Arthritis Res.* (2001) 3:48-53). Consistent with TNFα playing a critical role in the disease process, TNFα knock out mice fail to develop CpG-induced arthritis (Deng et al., *Arthritis Rheum.* (2000) 43:356-364; Ronaghy et al., *J. Immunology* (2002) 168:51-56). To evaluate whether suppressive ODN had an effect on TNFα production, BALB/c spleen cells were stimulated in vitro with CpG+suppressive ODN. As seen in FIG. 3, suppressive ODN reduced TNFα production in a dose-dependent manner, whereas control ODN had no effect.

To monitor the in vivo effect of suppressive ODN on TNF production, cytokine mRNA levels were measured in the joint. Consistent with earlier reports (Deng et al., *Arthritis Rheum.* (2000) 43:356-364; Ronaghy et al., *J. Immunology* (2002) 168:51-56; Kyburz et al., *Arthritis Rheum.* (2001) 44 (Suppl): S396), CpG ODN up-regulated local TNF mRNA levels (FIG. 3C, D). Co-administering suppressive ODN reduced TNF mRNA by >50% (p<0.003, FIG. 3).

Example 2

Systemic Effect of Stimulatory and Suppressive Oligodeoxynucleotides on the Induction of Inflammatory Arthritis Animals:

Female BALB/c mice were obtained from the Jackson Laboratories (Bar Harbor, Me.). The mice were used at 8-20 weeks of age and were housed under specific pathogen free conditions.

Oligonucleotides:

ODN used in this study had a phosphorothioate backbone, and were chemically synthesized. They contained <0.1 endotoxin units (EU) of endotoxin per mg of ODN, as assessed by a *Limulus amebocyte* lysate assay (QCL-1000, BioWhittaker). The sequence of the CpG ODN was GCTA-GACGTTAGCGT (SEQ. ID NO: 30), of the suppressive ODN: CCTCAAGCTTGAGGGG (SEQ. ID NO: 1), and of the control ODN: GCTAGATGTTAGCGT (SEQ ID NO: 31).

Experimental Protocols:

Arthritis was induced as previously described in Zeuner et al., *Arthritis Rheum*. (2002). Briefly 1 or 25 µg of ODN in 6 µl of PBS was injected into the knee joint using a 30 gauge needle. Joint swelling was measured in the coronal plane using a micrometer caliper (General Tools Mfg CO, NY, N.Y.). Mice were euthanized on day 4 and the knees fixed, decalcified, sectioned, and stained with hematoxylin/eosin prior to histologic examination. Scoring was performed by a blinded investigator using a scale of 0-4. 0=absence of inflammation, 1=sparse, localized perivascular infiltrate, 2=moderate infiltrate, 3=moderate-dense infiltrate with synovial hyperplasia, 4=dense infiltrate with pronounced synovial hyperplasia.

In some experiments, donor mice were injected intraperitoneally (i.p.) with 300 µg of ODN in PBS. A single cell suspension prepared from the spleens of these mice was prepared, and $20 \times 10^6$ transferred intravenously (IV) to naive littermate recipients. These spleen cells were enriched or depleted of various subpopulations using magnetic bead separation (Vario-Macs System, Miltenyi) as recommended by the manufacturer.

Statistical Analysis:

Differences between two groups determined using the Wilcoxon Rank Sum Test. Differences between multiple groups were evaluated using a two-tailed analysis of variance (ANOVA) on Ranks with Dunn's post test analysis. Differences in joint diameters were compared by repeated-measures ANOVA. A p value of <0.05 was considered significant. Data are presented as mean+/−SEM.

B. Effect of Systemic CpG ODN on Sensitivity of Joints to Inflammatory Stimuli

Previous studies established that intra-articular injection of bacterial DNA or CpG ODN induces arthritis in mice, characterized by an inflammatory cell infiltrate, perivascular accumulation of mononuclear cells, and hyperplasia of the synovial lining (Deng and Tarkowski, *Arthritis Rheum*. (2000) 43:356-364). Since reactive arthritis in humans is associated with infection of the gastrointestinal (GI) or genitourinary (GU) tract rather than the joint, we explored whether CpG DNA in the systemic circulation might alter the sensitivity of joints to inflammatory stimuli.

Figure 5:
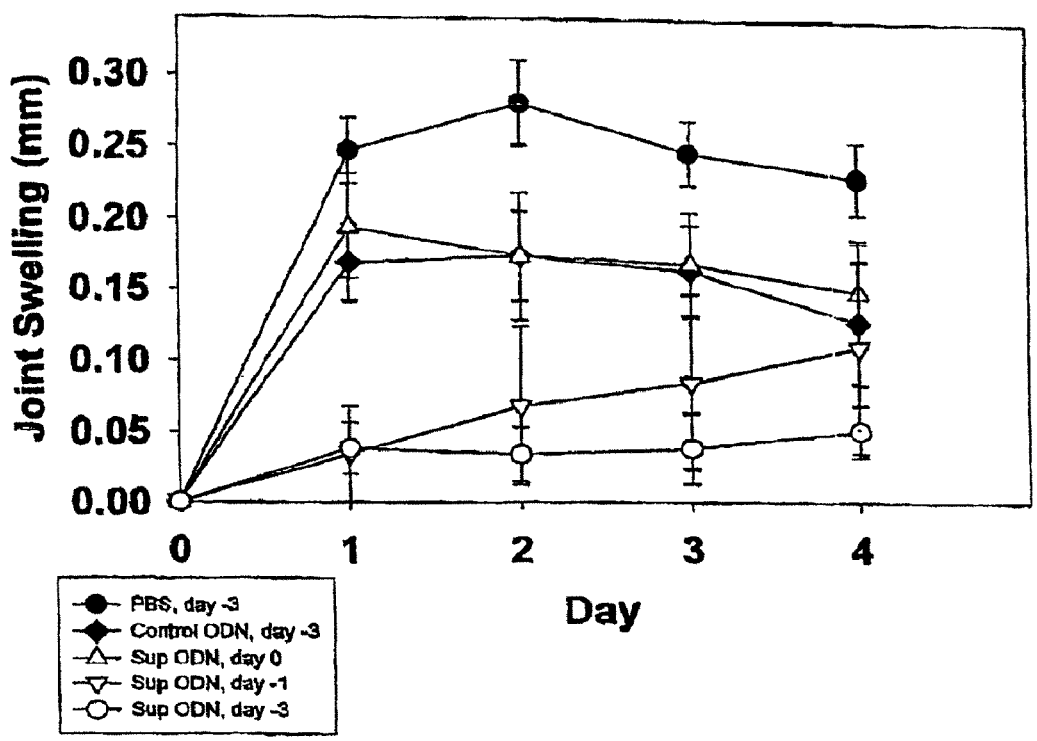
FIG. 5 is a graph showing that the local administration of suppressive ODNs reduces the pro-inflammatory effect of CpG ODN administration. Optimal suppression of CpG ODN-mediated joint inflammation is attained when the suppressive ODN are administered three days before the inflammatory challenge. Shown is the mean and standard error of measurement (SEM) of 10-11 mice/group pre-treated locally (intra-articularly) with suppressive ODN three days prior to CpG ODN challenge (open circles), suppressive ODN administered one day prior to CpG ODN challenge (open, inverted triangles), suppressive ODN administered at the time of the CpG ODN challenge (open triangles). The joint swelling of mouse knees injected with control ODN (black diamonds) or phosphate buffered saline (PBS; black circles) three days before the CpG serve as controls.

To examine this possibility, normal BALB/c mice were injected IP with 300 µg of CpG DNA, and then challenged with a sub-arthritogenic dose of local CpG ODN. As seen in FIG. 5, normal mice and mice treated with PBS or control ODN did not develop arthritis (no inflammation, no swelling) when injected with 1 µg of CpG. In contrast, animals pretreated with systemic CpG DNA developed significant joint swelling, a mononuclear cell infiltrate, and synovial hyperplasia when challenged with the same dose of CpG ODN. These changes were triggered by exposure to local CpG DNA, as no inflammation developed when the joints of systemically treated animals were injected with PBS.

These findings indicate that CpG DNA in the systemic circulation (perhaps released by dying bacteria in the GI or GU tract) can increase the host's susceptibility to the development local arthritis.

C. Systemic Administration of Suppressive ODN Reduces Susceptibility to Arthritis It has been demonstrated that suppressive ODN (containing motifs that selectively inhibit the immunostimulatory activity of CpG ODN) significantly reduce the swelling, synovial hyperplasia and leukocyte infiltration induced by CpG DNA. These effects were observed when suppressive ODN were injected directly into arthritic joints. Because systemic CpG DNA can increase the host's susceptibility to arthritis, suppressive ODN in the systemic circulation might lower this susceptibility.

Figure 6:
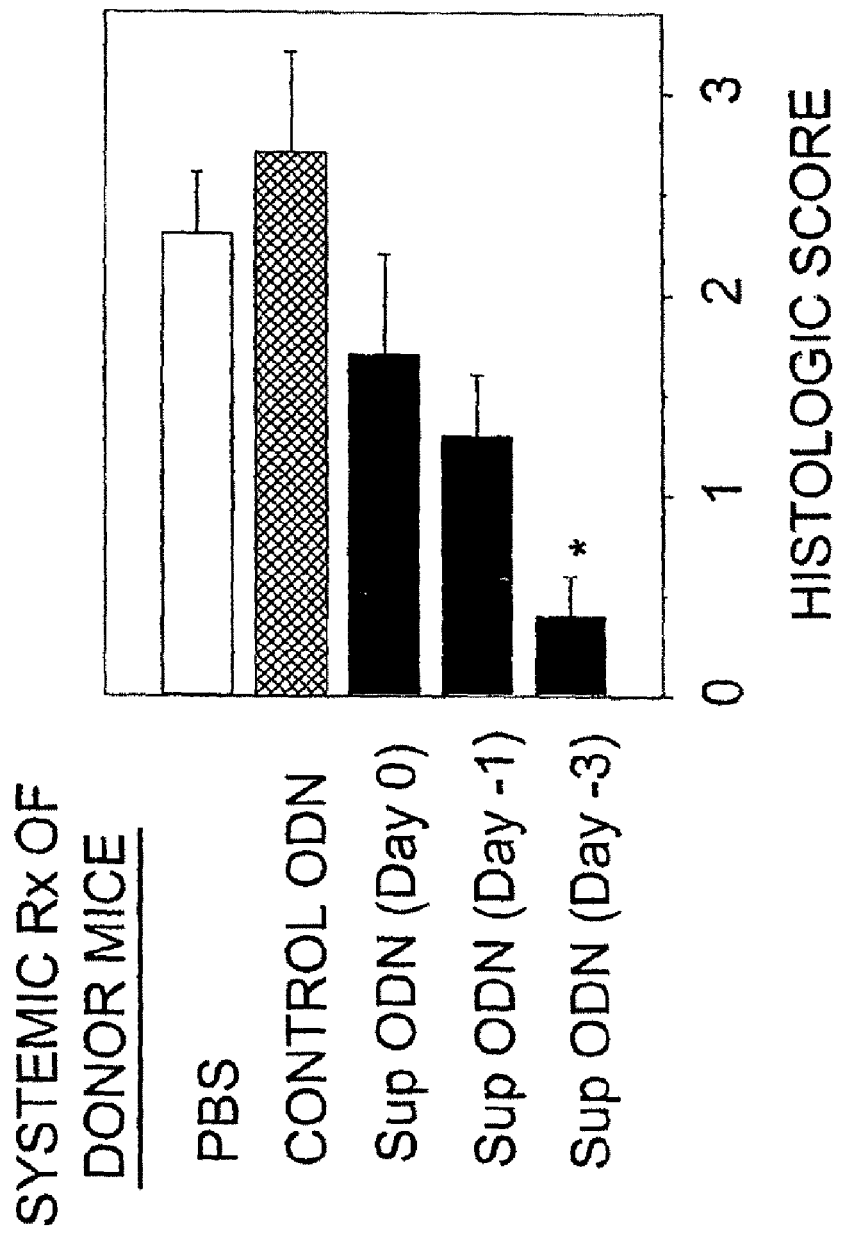
FIG. 6 is a graph showing that naive mice (and mice pre-treated with control ODN or PBS) developed severe arthritis following local CpG ODN challenge. In contrast, systemic administration of suppressive ODN three days prior to local CpG DNA challenge reduced joint swelling and inflammation by 80-85% ($p<0.029$). BALB/c mice were treated IP with 300 µg of suppressive ODN 0-3 days prior to the intra-articular injection of 25 µg CpG DNA. Consistent with previous studies, naive mice (and mice pre-treated with control ODN or PBS) developed severe arthritis following local CpG ODN challenge.
Figure 7:
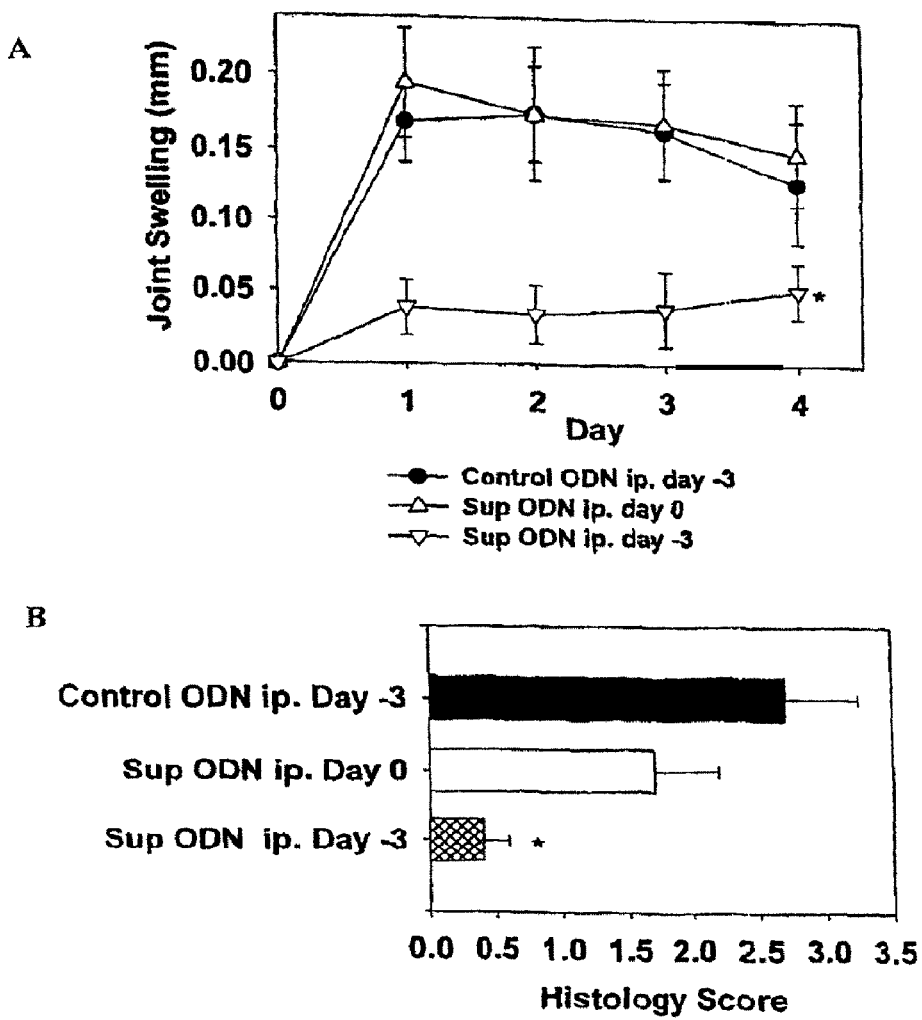
FIGS. 7A and 7B are a pair of graphs showing that systemic administration of suppressive ODN three days prior to local CpG DNA challenge reduced joint swelling and inflammation by 80-85% ($p<0.029$).

To test this hypothesis, BALB/c mice were treated intraperitoneally with 300 µg of suppressive ODN 0-3 days prior to the intra-articular injection of 25 µg CpG DNA. Consistent with previous studies, naive mice (and mice pre-treated with control ODN or PBS) developed severe arthritis following local CpG ODN challenge (FIG. 6). In contrast, systemic administration of suppressive ODN three days prior to local CpG DNA challenge reduced joint swelling and inflammation by 80-85% (FIG. 7; p<0.029). Unlike the situation with locally administered suppressive ODN, which reduced inflammation when administered up to two days after the induction of arthritis, suppressive ODN were effective systemically only if delivered several days prior to the induction of arthritis. These findings demonstrate that instead of blocking CpG induced arthritis locally, suppressive ODN in the systemic circulation activate a regulatory cascade that requires several days to mature.

D. Spleen Cells from Suppressive ODN Treated Mice Prevent CpG-Induced Arthritis

Figure 8A:
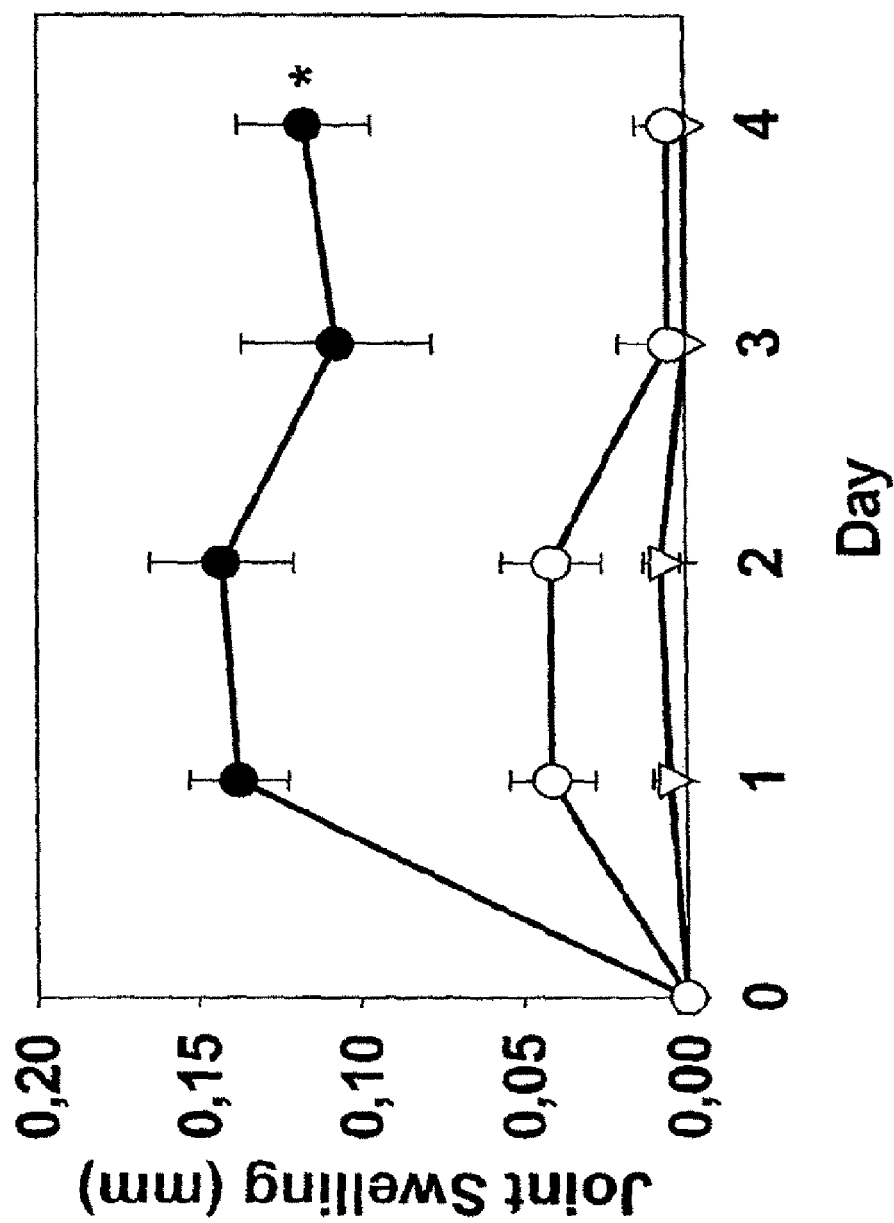
FIGS. 8A and 8B are a pair of graphs showing that systemically administered suppressive ODN elicit a population of regulatory cells that inhibit CpG-induced arthritis. As expected, spleen cells from untreated donors had no effect on the development of CpG-induced arthritis. By comparison, the transfer of $20\times10^6$ spleen cells from suppressive ODN treated donors significantly reduced joint swelling and inflammation in the recipients.
Figure 8B:
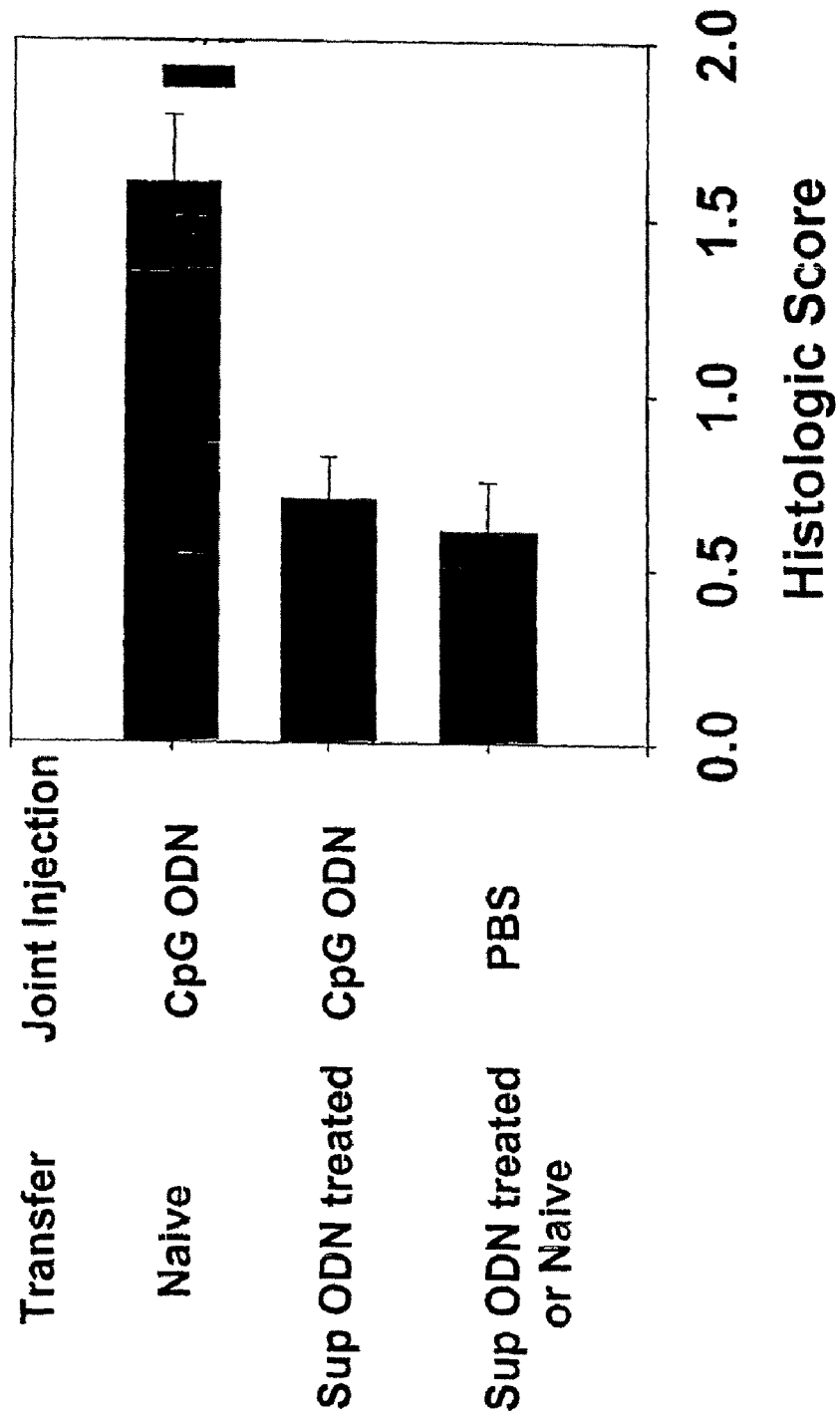

Spleen cells from mice treated systemically with suppressive ODN were transferred to naive controls, which were then injected with 25 µg of CpG DNA intra-articularly. As expected, spleen cells from untreated donors had no effect on the development of CpG-induced arthritis (FIG. 8). By comparison, the transfer of $20 \times 10^6$ spleen cells from suppressive ODN treated donors significantly reduced joint swelling and inflammation in the recipients. These findings indicate that systemically administered suppressive ODN elicit a population of regulatory cells that inhibit CpG-induced arthritis.

To define the time course over which these regulatory cells are generated, splenocytes were isolated from one to three days after treatment with suppressive ODN. Cells from animals treated with suppressive ODN for three days significantly inhibited CpG-induced arthritis, whereas splenocytes from animals exposed to suppressive ODN for shorter periods were progressively less effective.

Figure 9:
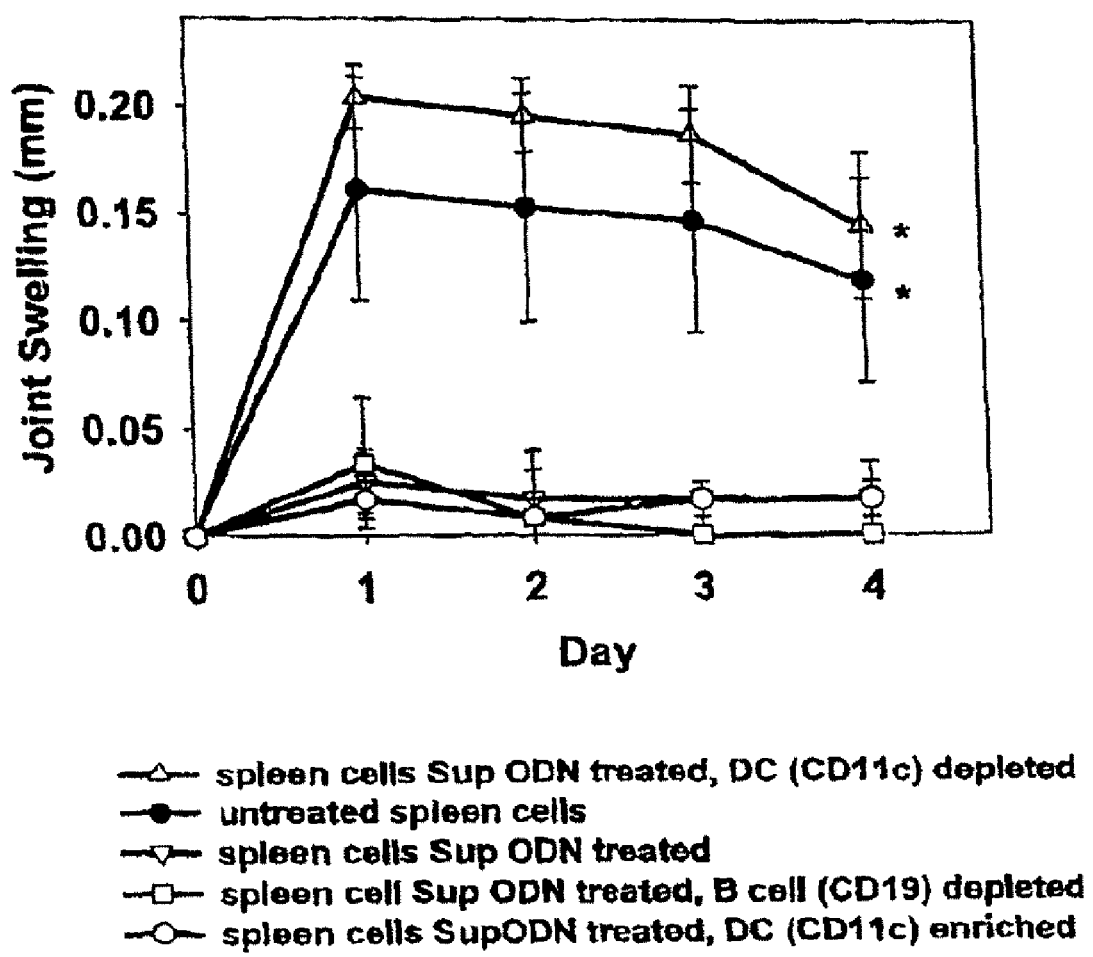
FIG. 9 is a graph showing that CD11c+ cells are responsible for the resistance to CpG-induced arthritis. Magnetic beads were used to deplete or enrich specific cell subpopulations from donor spleens. Depletion of CD19+ B cells, T cells, or NK cells had no effect on CpG-induced arthritis. However, removal of CD11c+ dendritic cells resulted in a complete abrogation of the suppressive activity of the transferred spleen cell population. Similarly, the transfer of only $5\times10^5$ CD11c+ enriched cells from suppressive ODN treated mice to normal recipients conferred resistance to CpG-induced arthritis.

To characterize the cell type responsible for this resistance to CpG-induced arthritis, magnetic beads were used to deplete or enrich specific cell subpopulations from donor spleens. Depletion of $CD19^+$ B cells, T cells, or NK cells had no effect on CpG-induced arthritis (FIG. 9). However, removal of $CD11c^+$ dendritic cells resulted in a complete abrogation of the suppressive activity of the transferred spleen cell population. Similarly, the transfer of only $5 \times 10^5$ CD11c+ enriched cells from suppressive ODN treated mice to normal recipients conferred resistance to CpG-induced arthritis.

Example 3

Repetitive Elements Present in Mammalian Telomeres Suppress Bacterial DNA-Induced Immune Activation This example demonstrates the ability of TTAGGG multimers to inhibit CpG-induced immune activation.

A. General Methods

Reagents

Endotoxin-free phosphorothioate or phosphodiester ODNs were chemically synthesized. 7-DG modified ODNs were synthesized using the 10-camphorsulphonyl-oxaziridine oxidization protocol recommended by the manufacturer (Glen Research, Sterling, Va.). Mammalian DNA was isolated from calf thymus and murine spleen (WIZARD® Genomic DNA purification kit, Promega Corporation, Madison, Wis.). E. coli was obtained from SIGMA-ALDRICH® (St. Louis, Mo.). Telomerase knockout mice were obtained from Johns Hopkins Univ., Baltimore, Md. All DNA obtained from commercial providers was re-purified to eliminate endotoxin (<0.1 U/mg). Double stranded DNA was converted to single stranded DNA by heat denaturing at 95° C. for five minutes followed by cooling on ice. BAL-31 (NEW ENGLAND BIOLABS®, Beverly, Mass.) digestion of CT DNA was continued for 2 hours at 30° C. according to manufacturer's recommendations. At the end of the incubation, the enzyme was inactivated at 65° C. for 10 minutes. Plasmid encoding for 1.6 kb long TTAGGG repeat was obtained from University of Texas Southwestern Medical Center, Dallas, Tex. Non-telomere coding plasmid was from Vical (San Diego, Calif.).

Mice

Specific pathogen-free male BALB/c mice (Jackson Laboratories, Bar Harbor, Me.) were housed in sterile micro-isolator cages in a barrier environment and injected intraperitoneally with 400 μg of CpG ODN plus 200 μg of suppressive or control ODN. Spleen cells were harvested 6 hours later and monitored for cytokine production after 36 hours. In order to measure the pEPO transgene expression levels, female Balb/c mice (4-6 weeks old) were injected with 30 μg of pVRmEPO (Vical, San Diego, Calif.) plasmid in sterile saline into the anterior tibialis muscle alone or in combination with 50 μg of control or suppressive ODN. Hematocrits were measured as described (Tripathy et al., *Proc Natl Acad Sci USA*. 93:10876-80, 1996) on blood collected by tail vein puncture.

Cytokine and IgM ELISA Assays

Immulon 2 microtiter plates (Dynex Technologies Inc., Chantilly Va.) were coated with anti-cytokine or anti-IgM antibodies (Pharmingen, San Diego Calif.) and then blocked with PBS—1% bovine serum albumin (BSA). Serially diluted culture supernatant or serum was added for two hours. Cytokine was detected using biotinylated anti-cytokine antibody followed by phosphatase-streptavidin (Pharmingen) whereas bound IgM was detected using phosphatase-conjugated anti-IgM antibodies (Southern Biotechnology Associates, Birmingham, Ala.) as described.

Detection of Co-Stimulatory Molecule Expression by FACS $2 \times 10^6$ spleen cells/ml were incubated with ODN for 24 hours. Cells were washed, fixed with 5% paraformaldehyde for 15 minutes, and stained with PE-labeled anti CD-40, anti CD-86, and anti ICAM-1 (Pharmingen, San Diego, Calif.) for 30 minutes at room temperature. Cells were washed, re-suspended in PBS/BSA (supplemented with Azide), and analyzed by fluorescence activated cell sorting (FACSort, Becton Dickinson, San Jose, Calif.).

Cytokine RT-PCR

Spleen cells were isolated 6 hours after CpG ODN injection. Total RNA was extracted, reverse-transcribed, and amplified in a standard PCR reaction for 24 cycles using primers specific for murine interleukin-6 (IL-6), interleukin-12 (IL-12), and interferon (IFN) as previously described. PCR amplified material was separated on 1.5% agarose gels and visualized under ultraviolet (UV) light after ethidium bromide staining.

In Vitro DNA-PK Assay

DNA-dependent protein kinase activity was measured as recommended by the manufacturer (Promega, Madison, Wis.). Briefly, 20 units of affinity-purified human DNA—PKcs and 10 nM of ODN were incubated with 0.4 mM biotinylated peptide substrate and $P_{32}$-ATP for 5 minutes at 30° C. in reaction buffer. Phosphorylated substrate was captured on streptavidin coated SAM membranes (Promega), and measured in a scintillation counter.

Cell Transfection and Luciferase Assay

HEK 293 ($5 \times 10^4$) cells (ATCC, Manassas, Va.) were transfected with 0.8 μg of vector plasmid (pClneo, Promega, Madison, Wis.), pClneo-mTLR9, plus 0.1 μg of p5xNF— kB-luc (Stratagene, Lajolla, Calif.) and 0.1 μg of pSV-beta-galactosidase (Promega) and incubated overnight at 37° C. The cells were then stimulated with indicated ODN for 24 h. Cells were then harvested and luciferase assay was performed as recommended by the manufacturer (Promega). Beta-galactosidase activity was used to normalize the data.

Measurement of Circular Dichroism

A Jasco J-720A spectropolarimeter was used to measure the circular dichroism of ODN (50 g/ml in 0.1×PBS). Data is expressed as the mean peak ellipticity (mdeg/abs) of 5-10 readings/sample in the 260-270 nm range.

Statistical Analysis

In vitro assays were performed in triplicate on at least three different spleen cell preparations. All in vivo experiments were performed on a minimum of five to ten mice/group. Statistical significance was evaluated using Student's t test. Correlation analysis is computed by linear correlation analysis between CD data vs % suppression.

B. TTAGGG Multimers Inhibit CpG-Induced Immune Activation

The ability of TTAGGG multimers to inhibit CpG-induced immune activation was tested. Initial experiments showed that ODNs containing suppressive motifs inhibit CpG-induced immune activation in a dose-dependent fashion (FIG. 10A).

ODNs containing the largest number of TTAGGG repeats (n=4) were the most suppressive (p<0.001; FIG. 10B). Single TTAGGG hexamers were suppressive only when incorporated into larger ODNs (≧10 bases in length), and were somewhat less active than TTAGGG multimers. TTAGGG motifs were suppressive both in cis and in trans; they inhibited immune activation when present on the same or on a different strand of DNA than that expressing the stimulatory CpG sequence (FIGS. 10C and D). This inhibitory activity was exquisitely specific: even high concentrations of suppressive ODNs had no effect on mitogen-induced immune responses (FIG. 10D), indicating that suppressive ODN were neither toxic nor non-specifically immunosuppressive.

C. Suppression is Mediated by Poly-G Sequences

The bases contributing to this suppressive activity were identified by systematically modifying ODNs containing single TTAGGG motifs. Substitutions outside the telomere-derived sequence did not significantly affect suppression.

Replacing multiple bases in the TTA region of the TTAGGG motif also had little effect on the suppressive activity (FIG. 10E). In contrast, replacing two or more of the Gs in this motif substantially reduced the ODN's ability to block CpG-induced immune activation (FIG. 10E). These results indicate that suppression is mediated by the poly-G sequence itself, or the two-dimensional structure imposed by that sequence.

D. Suppression is Mediated by the Two-Dimensional Structure of the Motifs

To differentiate between these alternatives, individual Gs were replaced by 7-deaza guanosine (7-DG) analogues. These 7-DG substitutions did not alter the base sequence of the ODN but did prevent Hoogsteen hydrogen bonding between guanosines, thereby reducing G tetrad formation (Hurley et al., *Trends Pharmacol. Sci.* 21:136-142, 2000; Lilley et al., *EMBO J.* 13:993-1001, 1994). The resultant loss in secondary structure is reflected by a loss in circular dichroism (Lilley et al., *EMBO J.* 13:993-1001, 1994). ODNs capable of forming G tetrads typically have peak CD values >2, while those without such secondary structure have circular dichroism values <1.4 (FIG. 10).

Figure 11:
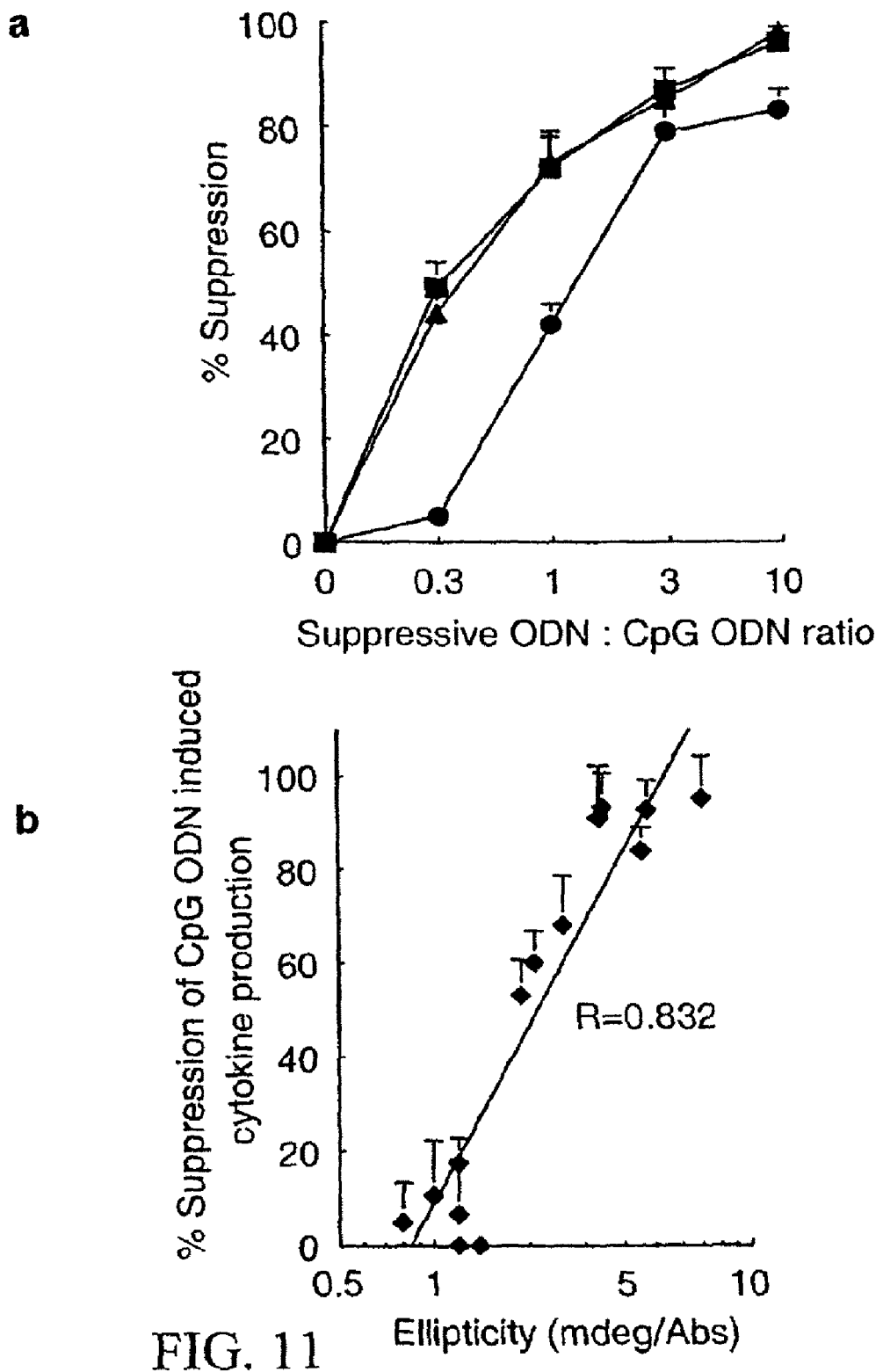
FIG. 11 is a pair of graphs showing that G-tetrad-forming suppressive ODNs selectively suppress CpG-induced immune activation.

Introducing a 7-DG substitution significantly reduced an ODN's ability to form a G-tetrad and to mediate suppression ($p<0.001$, FIG. 11). To confirm that G-tetrad formation was critical to suppression, ODNs were synthesized that lacked the TTAGGG motif but still formed G-tetrads. These novel ODNs suppressed CpG ODN and bacterial DNA induced immune stimulation by >90% ($p<0.001$; FIG. 10F). Indeed, there was a consistent correlation between G-tetrad forming ability and suppressive activity ($R=0.832$, FIG. 11B).

E. Mechanism of Suppressive ODN Activity

The mechanism by which suppressive ODNs inhibit immune activation was explored. Both bacterial DNA and CpG ODN stimulated DNA-dependent protein kinase activity in vitro. Of particular interest, this activity was specifically blocked by TTAGGG multimers and other G tetrad forming ODN, but not their 7-DG modified analogues. These findings indicate that suppressive motifs inhibit CpG-dependent DNA-$PK_{os}$ activation of immune cells. In contrast, suppressive ODNs did not block the binding or internalization of CpG ODNs mediated by Toll-like receptor 9.

Example 4

Effect of Suppressive ODNs on CpG-induced Immune Action

This example demonstrates the kinetics, magnitude, and nature of the immune inhibition elicited by suppressive motifs. Previous studies established that the immunostimulatory activity of CpG DNA can be reversed several hours later either by removing the stimulatory DNA or adding suppressive DNA. The same cells that interact with stimulatory motifs also recognize suppressive motifs. When both sequence types are present on the same strand of DNA, recognition proceeds in a 5'->3' direction. Suppression is generally dominant over stimulation, although a motif in the 5' position can interfere with recognition of a motif immediately downstream. Understanding the rules governing cellular responses to stimulatory and suppressive motifs facilitates the design of ODN for therapeutic uses.

A. General Methods

Animals:

Female Balb/c mice were obtained from the Jackson Laboratories (Bar Harbor, Me.). The mice were housed under specific pathogen free conditions, and used at 8-20 weeks of age. All studies involved protocols approved by the CBER Animal Care and Use Committee.

Oligodeoxynucleotides:

Studies utilized phosphorothioate modified ODNs that were synthesized at the CBER core facility Verthelyi, D., et al., *J Immunol* (2001) 166:2372. The following ODNs were used: immunostimulatory ODN1466 (TCAACGTTGA; SEQ. ID NO: 26) and ODN1555 (GCTAGACGTTAGCGT; SEQ. ID NO: 27), control ODN1471 (TCAAGCTTGA; SEQ. ID NO: 28) and ODN1612 (GCTAGAGCTTAGGCT; SEQ. ID NO: 29), suppressive ODN1502 (GAGCAAGCTGGACCTTCCAT; SEQ. ID NO: 20) and ODNH154 (CCTCAAGCTTGAGGGG; SEQ. ID NO: 1). Underlined bases represent the 10-mer sequences that were incorporated into complex multi-determinant ODN used in some experiments. There was no detectable protein or endotoxin contamination of these ODN.

Mammalian DNA was purified from BALB/c spleens (Wizard Genomic DNA purification kit, Promega, Madison, Wis.). *E. coli* DNA was obtained from Gibco BRL (Rockville, Md., USA). Endotoxin contamination in these preparations was <0.1 U/ml after purification Klinman, D. M., et al., *J. Immunol.* (1997) 158:3635. Double stranded DNA (dsDNA) was converted to single stranded DNA (ssDNA) by heat denaturing at 95° C. for 5' followed by immediate cooling on ice.

Cytokine ELISA Assays:

Single spleen cell suspensions were washed three times and re-suspended in RPMI-1640 supplemented with 5% heat inactivated fetal calf serum (FCS), 1.5 mM L-glutamine and 100 U/ml of penicillin/streptomycin. $5 \times 10^5$ cells/well were cultured in flat-bottomed microtiter plates (Costar, Corning, N.Y.) with 1 µM ODN for 18-24 h. Culture supernatants were collected, and cytokine levels measured by ELISA. In brief, 96 well Immulon H2B plates were coated with cytokine-specific antibodies and blocked with PBS 1% BSA as previously described in Klinman and Nutman, *Current Protocols in Immunology* (1994), Coligan, Kruisbeek, Margulies, Shevach, and Strober, eds., Greene Publishing Associates, Brooklyn, N.Y. Culture supernatants were added, and bound cytokine detected by the addition of biotin labeled secondary antibodies followed by phosphatase-conjugated avidin and a phosphatase-specific colorimetric substrate (PNPP, Pierce, Rockford, Ill.). Standard curves were generated using recombinant cytokines. The detection limit for these assays was: 0.8 U/ml for IFNγ, 0.1 ng/ml for IL-6 and 0.1 ng/ml for IL-12. All assays were performed in triplicate.

Cytokine-Specific ELIspot Assays:

A single spleen cell suspension prepared in RPMI 1640 plus 5% FCS was serially diluted onto plates pre-coated with anti-cytokine antibodies. (see Klinman and Nutman, *Current Protocols in Immunology* (1994), Coligan, Kruisbeek, Margulies, Shevach, and Strober, eds., Greene Publishing Associates, Brooklyn, N.Y.). Cells were incubated with 1 µM ODN at 37° C. for 8-12 hours, and their secretion of cytokine detected colorimetrically as previously described (Klinman and Nutman, *Current Protocols in Immunology* (1994), Coligan, Kruisbeek, Margulies, Shevach, and Strober, eds., Greene Publishing Associates, Brooklyn, N.Y.).

Cell-Surface Binding and Internalization of ODN:

Spleen cells ($2 \times 10^6$/ml) were incubated with 1 µM of unlabeled and/or fluorescent-labeled ODN for 10 minutes at 4° C. (binding experiments) or at 37° C. for 1 hour (uptake experiments Gursel et al., *J. Leuko. Biol.* (2001). Cells were washed, fixed, and analyzed by FACScan (Becton Dickinson, San Jose, Calif.).

Statistical Analysis:

Statistically significant differences between two groups were determined using the Wilcoxon Rank Sum Test. When comparing more than two groups, differences were determined using a 2-tailed non-parametric ANOVA with Dunn's post-test analysis. A p value of <0.05 was considered significant.

B. Mammalian DNA Suppresses CpG DNA-Induced Immune Activation

Figure 12:
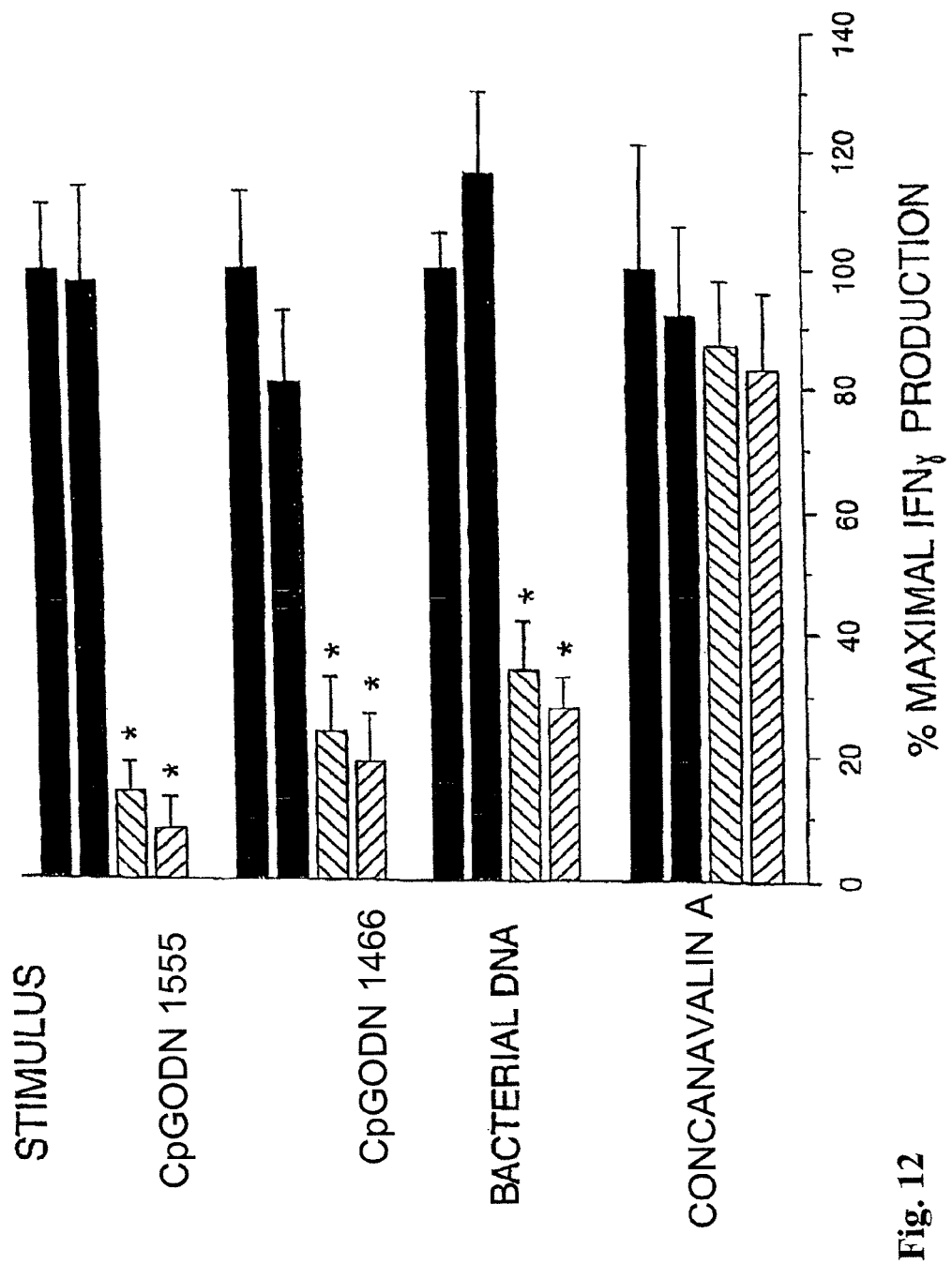
FIG. 12 is a graph showing the effect of suppressive ODN on CpG DNA and Concavalin A induced IFNγ production. BALB/c spleen cells were stimulated with 1 µM CpG ODN (ODN1555, ODN1466), 50 µg/ml of bacterial DNA, or 5 µg/ml Con A. The response of these cultures was compared to cells co-stimulated with 1 μM of control ODN1612, suppressive ODN1502 or suppressive ODNH154. The number of IFNγ secreting cells was determined by ELIspot after 18 hours. Data represent the average+standard deviation (SD) of triplicate cultures. The experiment was repeated three times with similar results.

Single stranded bacterial DNA and synthetic ODN containing unmethylated CpG motifs stimulate immune cells to mature, proliferate and produce cytokines, chemokines, and immunoglobulins. (Klinman et al., *Proc. Natl. Acad. Sci. USA* (1996) 93:2879; Roman et al., *Nature Medicine* (1997) 3:849; Roman et al., (1997) *Nature Medicine* 3:849; Yamamoto et al., (1992) *J. Immunol.* 148:4072; Krieg et al., (1995) *Nature* 374:546). These effects can be blocked by "poly-G" and/or "GC" rich DNA motifs (Krieg et al., (1998) *Proc. Natl. Acad. Sci.* 95:12631; Pisetsky et al., (1995) NY Acad. Sci. 772:152). Scores of ODNs were synthesized and tested, and eventually several were identified that selectively inhibited CpG-induced immune responses. The two most active of these suppressive ODN (ODN1502 and ODNH154) were selected for detailed study. As seen in FIG. 12, suppressive ODN blocked a majority of the IFNγ production induced by bacterial DNA or CpG ODN (p<0.01). Suppressive ODN were neither toxic nor broadly immunosuppressive, as they did not interfere with the mitogenic activity of LPS or Concavalin A (Con A; FIG. 12).

Figure 13:
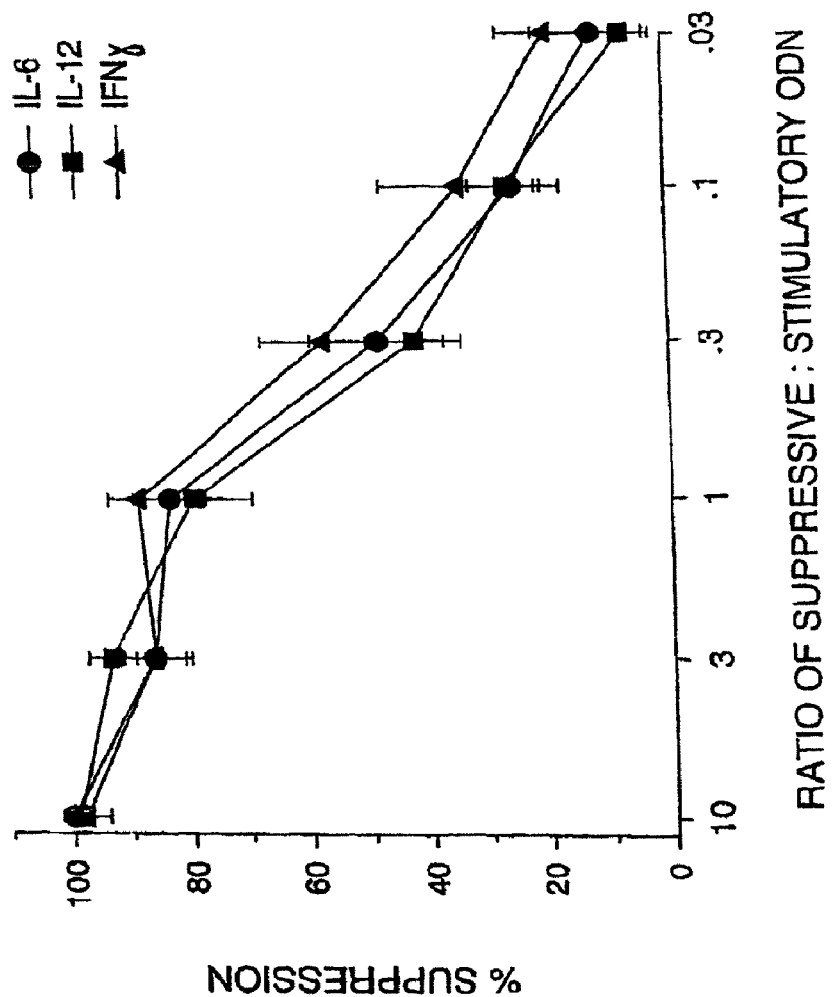
FIG. 13 is a graph showing the concentration effects of suppressive ODN. BALB/c spleen cells were stimulated with 1 μM CpG ODN1555 or ODN1466 plus increasing amounts of suppressive ODN1502 or ODNH154. Cytokine levels in culture supernatants were measured by Enzyme-Linked Immunosorbent Assay (ELISA) after 24 hours. Results represent the mean±SD of 4 different experiments.
Figure 14:
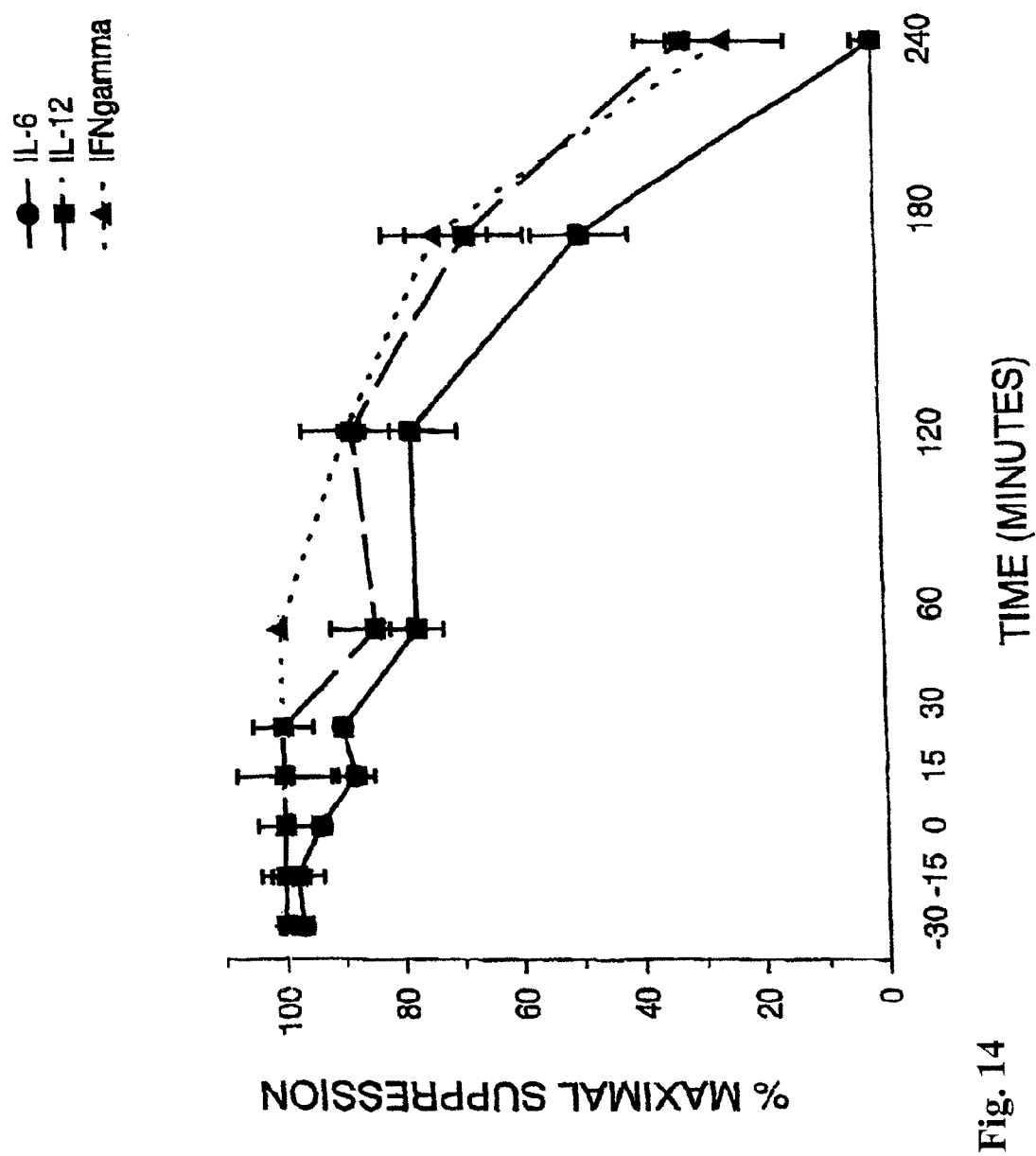
FIG. 14 is a graph showing the kinetics of suppressive ODN. BALB/c spleen cells were stimulated with 1 μM CpG ODN1555. At various times, 1 μM suppressive ODN1502 was added. Cytokine levels in culture supernatants were measured by ELISA after 24 hours. Results represent the mean of two independent experiments.

The activity of suppressive ODNs was concentration dependent, with 50% suppression being achieved at a suppressive to CpG ODN ratio of approximately 1:3 (FIG. 13). To examine the kinetics of this inhibition, suppressive ODN were added to BALB/c spleen cells at various times after CpG-induced stimulation. Maximal inhibition was observed when suppressive ODN were co-administered with CpG ODN, although statistically significant inhibition persisted when suppressive ODN were added up to 3 hours later (FIG. 14). These findings indicate that CpG induced immune activation is an ongoing process, and can be inhibited after the stimulatory signal is delivered.

Figure 15:
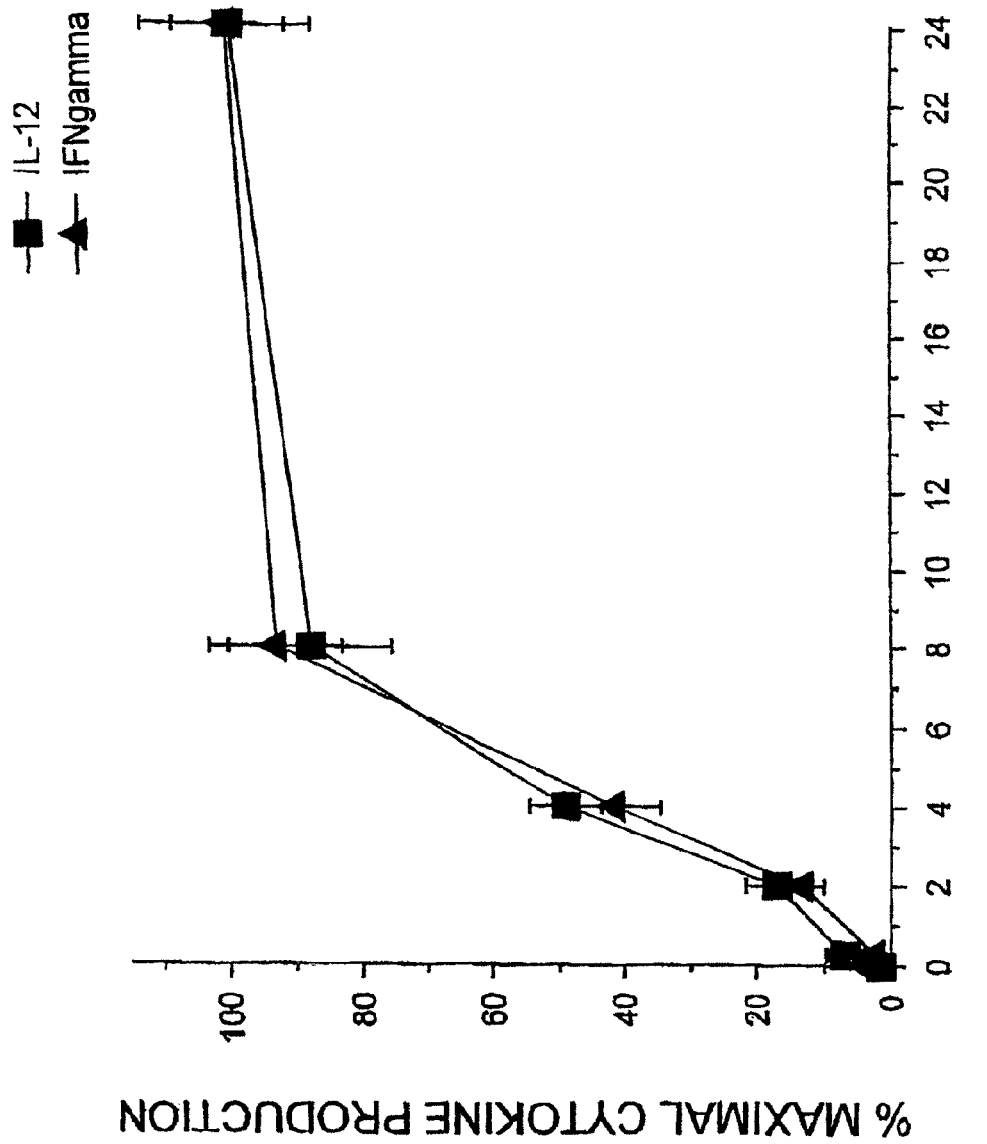
FIG. 15 is a graph showing the effect of removing CpG ODN from cultured cells. 1 μM of CpG ODN1555 was added to BALB/c spleen cells at time (T)=0. The cells were washed free of this ODN after various incubation periods. IFNγ and IL-12 levels in culture supernatants were measured by ELISA after 24 hours. Results represent the average+SD of duplicate cultures. Similar results were obtained in studies of CpG ODN1466.

To test this conclusion, spleen cells were incubated with CpG ODN for various periods and cytokine production analyzed after 24 hours. Cells stimulated with CpG DNA for 8 hours produced 90% as much cytokine as cells stimulated continuously for 24 hours (FIG. 15). Cells treated with CpG ODN for only 4 hours produced half as much cytokine, while cells treated with CpG DNA for <2 hours showed only minimal activation (FIG. 15). These findings support the conclusion that CpG-induced cellular activation is reversible for several hours.

Figure 16:
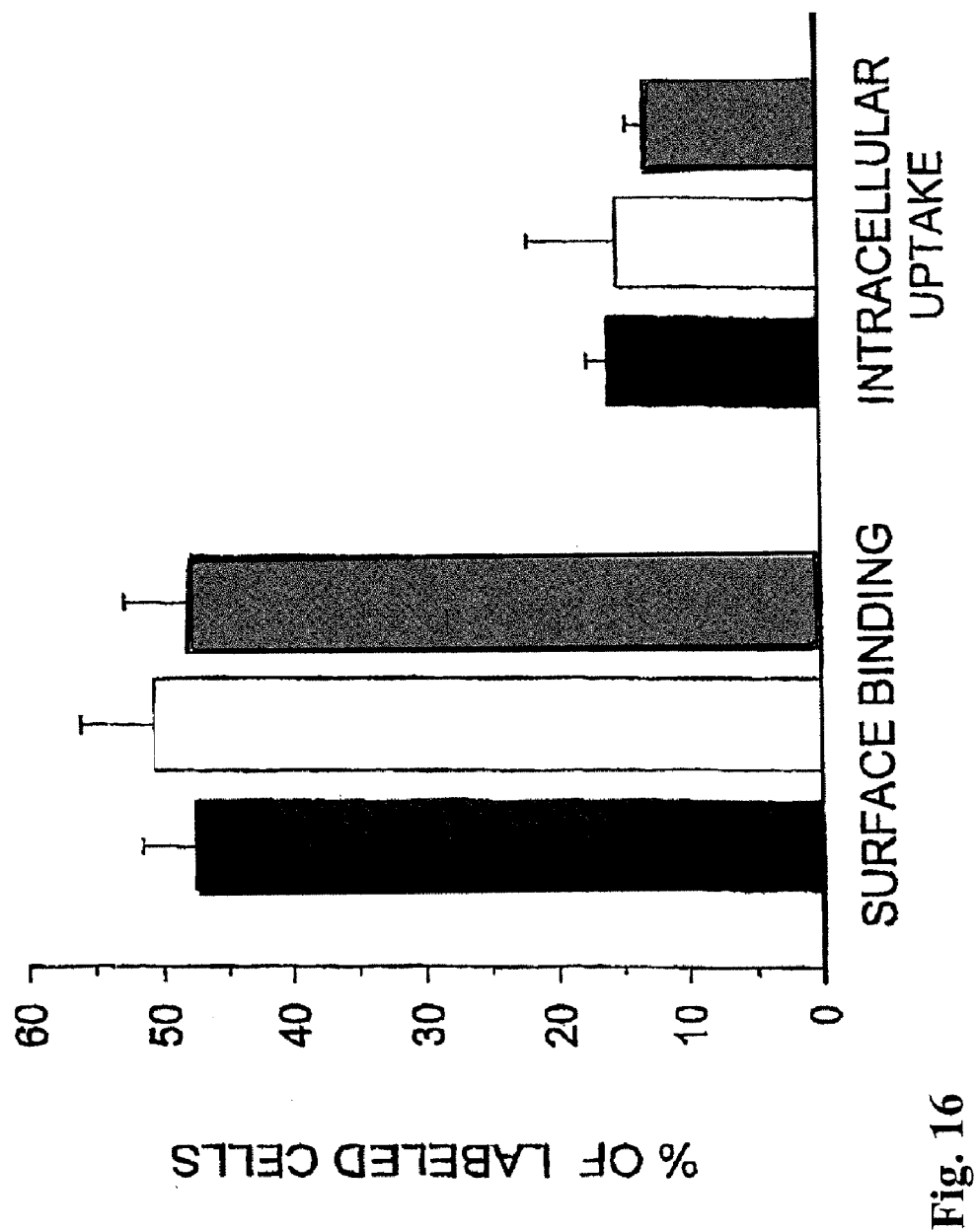
FIG. 16 is a graph showing that suppressive ODN do not block the binding or uptake of CpG ODN. BALB/c spleen cells were incubated with 1 μM of CpG ODN1555 (black bar) plus 1 μM of suppressive ODN1502 (grey bar) or control ODN1612 (white bar). The percent of cells that bound or internalized the CpG ODN was determined by FACS. Similar results were obtained using CpG ODN1466, suppressive ODNH154 and control ODN1471.

C. Suppressive ODNs do not Block CpG ODN Uptake or Induce the Production of Inhibitory Factors The results described above indicate that CpG-induced immune activation can be reversed either by adding suppressive ODNs or by removing stimulatory ODNs. This indicates that suppressive ODNs block the ongoing uptake of CpG DNA. Yet FACS analysis demonstrated that neither cell surface binding nor internalization of fluorescein isothiocyanate (FITC)-labeled CpG ODN was significantly reduced by suppressive ODN at concentrations that blocked cytokine production by approximately 75% (FIG. 16).

The possibility that suppressive motifs might induce the production of a factor that blocks CpG-dependent immune activation was then investigated. Initial studies established that BALB/c spleen cells pre-incubated with suppressive ODN remained unresponsive to CpG-induced stimulation for several hours (Table I, line 3). If this non-responsive state was mediated by a soluble factor (or inhibitory cell-cell interactions) then cells pre-treated with suppressive ODN should block CpG-induced stimulation of naive spleen. As seen in Table I, cells treated with suppressive ODN had no significant effect on CpG dependent cytokine production by fresh splenocytes.

TABLE I

Effect of mixing cells treated with suppressive versus stimulatory ODN

| Cells pre-treated with suppressive ODN | ODN added during | | % maximal cytokine production | |
|---|---|---|---|---|
| | Fresh cells | culture | IL-6 | IL-12 |
| − | + | CpG | 100 ± 13 | 100 ± 6 |
| − | + | Control | 3 ± 2 | 7 ± 2 |
| + | − | CpG | 9 ± 6 | 6 ± 2 |
| + | − | Control | 0 ± 0 | 0 ± 0 |
| + | + | CpG | 86 ± 16 | 105 ± 12 |
| + | + | Control | 0 ± 0 | 0 ± 0 |

BALB/c spleen cells were treated with 1 μM suppressive ODN$_{1502}$ for 2 hours and then washed (first column). These cells were added to naive splenocytes (second column) plus 1 μM of control ODN$_{1471}$ or CpG ODN$_{1555}$. IL-6 and IL-12 levels in culture supernatants were measured by ELISA after 18 hours. Results represent the average + SD of triplicate assays, each standardized to the response induced by bacterial DNA (62 pg/ml IL-6; 134 pg/ml IL-12).

D. Cellular Recognition of Suppressive Versus Stimulatory Motifs

The above studies establish that suppressive motifs on one strand of DNA block the immune activation induced by stimulatory motifs on a different strand (trans suppression). To better understand the interaction between suppressive and stimulatory motifs, ODNs containing both were synthesized. In the simplest case, a 20-mer was constructed in which a CpG motif was placed immediately 5' to a suppressive motif (referred to as [CpG-Sup] ODN).

Experiments showed that this ODN was stimulatory, triggering murine spleen cells to produce IL-6, IL-12 and IFNγ to the same extent as an ODN of the same length in which the suppressive motif was replaced by a 'control' sequence (one that was neither stimulatory nor suppressive, Table II). [CpG-Sup] ODNs also failed to block the immune activation induced by an independent CpG ODN (Table II). These results indicate that a suppressive motif is inactive when located immediately 3' to a CpG motif on the same strand of DNA. Similar results were obtained in studies of additional [CpG-Sup] ODNs that utilized different stimulatory and suppressive motifs.

TABLE II

Effect of motif position on immunostimulatory activity

| Location of motifs | # of cytokine secreting cells | | |
|---|---|---|---|
| (5' → 3') | IL-6 | IL-12 | IFNg |
| CpG ODN * | 79 ± 13 | 1980 ± 230 | 260 ± 40 |
| [CpG − Sup] ODN* | 72 ± 14 | 2080 ± 480 | 230 ± 60 |
| [Sup − CpG] ODN | 0 ± 0 | 140 ± 30 | 0 ± 0 |
| [CpG − Cont] ODN* | 64 ± 12 | 2210 ± 130 | 284 ± 34 |
| [Cont − CpG] ODN* | 80 ± 11 | 1942 ± 88 | 238 ± 28 |
| [Cont − Sup] ODN | 8 ± 2 | 184 ± 34 | 36 ± 8 |
| [CpG − Sup] ODN + Sup ODN | 4 ± 2 | 226 ± 38 | 28 ± 6 |

TABLE II-continued

Effect of motif position on immunostimulatory activity

| Location of motifs | # of cytokine secreting cells | | |
|---|---|---|---|
| (5' → 3') | IL-6 | IL-12 | IFNg |
| [Sup – CpG] ODN + CpG ODN* | 7 ± 3 | 250 ± 32 | 34 ± 9 |

$10^6$ BALB/c spleen cells were co-incubated with 1 μM of each ODN. Complex ODN (20 bp in length) were constructed from 10-mers containing suppressive (Sup), stimulatory (CpG) or control (Cont) motifs. The number of cytokine secreting cells/$10^6$ was determined by ELIspot after 24 hours of stimulation. Equivalent results were derived using combinations of motifs derived from two different stimulatory (ODN$_{1555}$ and ODN$_{1466}$), contol (ODN$_{1471}$ and ODN$_{1612}$) and suppressive (ODN$_{1502}$ and ODN$_{H154}$) ODN. Results represent the average ± SD of triplicate assays involving at least two ODN of each type.
*Stimulatory ODN, p < .05.

$10^6$ BALB/c spleen cells were co-incubated with 1 μM of each ODN. Complex ODN (20 bp in length) were constructed from 10-mers containing suppressive (Sup), stimulatory (CpG) or control (Cont) motifs. The number of cytokine secreting cells/$10^6$ was determined by ELIspot after 24 hours of stimulation. Equivalent results were derived using combinations of motifs derived from two different stimulatory (ODN$_{1555}$ and ODN$_{1466}$), control (ODN$_{1471}$ and ODN$_{1612}$) and suppressive (ODN$_{1502}$ and ODN$_{H154}$) ODN. Results represent the average±SD of triplicate assays involving at least two ODN of each type.

*Stimulatory ODN, p<0.05.

To better understand this phenomenon, longer ODNs were synthesized in which the CpG and suppressive motifs were separated by progressively longer CT spacers. Adding a 5 base spacer generated an ODN that was still stimulatory (Table III). However, separating the motifs by >10 bases yielded ODNs that were suppressive, since they blocked the stimulatory activity of co-administered CpG ODNs (Table III).

TABLE III

Effect of distance between motifs on ODN activity

| ODN | Cytokine producing cells (% maximum) | | |
|---|---|---|---|
| | IL-6 | IL-12 | IFNg |
| CpG ODN* | 100 ± 11 | 100 ± 7 | 100 ± 10 |
| CpG ODN* + Cont ODN | 97 ± 14 | 98 ± 9 | 100 ± 17 |
| CpG ODN* + Sup ODN | 16 ± 6 | 21 ± 6 | 18 ± 5 |
| [CpG – Sup] ODN* | 87 ± 12 | >100 ± 14 | 92 ± 14 |
| [CpG – 5 bases – Sup] ODN* | >100 ± 4 | >100 ± 21 | >100 ± 22 |
| [CpG – 10 bases – Sup] ODN | 38 ± 6 | 64 ± 15 | 42 ± 7 |
| [CpG – 20 bases – Sup] ODN | 7 ± 4 | 48 ± 13 | 24 ± 8 |
| [CpG – 20 bases – Cont] ODN* | 94 ± 7 | >100 ± 14 | 99 ± 11 |
| [Sup – CpG] ODN | 0 ± 0 | 0 ± 0 | 0 ± 0 |
| [Sup – 20 bases – CpG] ODN | 8 ± 5 | 9 ± 3 | 2 ± 1 |
| [CpG – Sup] ODN* + CpG ODN* | >100 ± 16 | >100 ± 15 | 98 ± 13 |
| [CpG – 5 bases – Sup] ODN* + CpG ODN* | >100 ± 18 | >100 ± 11 | 98 ± 20 |
| [CpG – 10 bases – Sup] ODN + CpG ODN* | 58 ± 7 | 75 ± 9 | 66 ± 9 |
| [CpG – 20 bases – Sup] ODN + CpG ODN* | 27 ± 5 | 26 ± 10 | 30 ± 8 |
| [Sup – CpG] ODN + CpG ODN* | 9 ± 4 | 11 ± 4 | 8 ± 5 |
| [Sup – 20 CT – CpG] ODN + CpG ODN* | 5 ± 1 | 9 ± 3 | 13 ± 2 |

BALB/c spleen cells were stimulated in vitro with 1 μM of each ODN, and the number of cells activated to secrete cytokine determined 8 hours later by ELIspot. The percent of cells activated to secrete cytokine was calculated by the formula: (# of cells activated by test ODN) – (background)/(# of cells activated by CpG ODN) – (background) × 100%.

Two different control (ODN$_{1471}$, and ODN$_{1612}$), CpG (ODN$_{1466}$ and ODN$_{1555}$) and suppressive (ODN$_{1502}$ and ODN$_{H154}$) ODN gave similar results in these experiments.

Results represent the average of 2-4 assays/data point. Table II shows typical numbers of cytokine secreting cells/$10^6$.

*Stimulatory ODN, p < .05.

The trivial possibility that the CT spacer somehow reduced CpG activity was eliminated by substituting a "control" motif for the 3' suppressive motif. The resulting ODNs were fully stimulatory (Table III).

The impact of placing a suppressive motif 5' to a CpG motif was then examined. ODNs with a suppressive motif in the 5' position induced little or no immune activation, even when the CpG motif was shifted up to 20 bp downstream from the suppressive motif (Tables II and III). This lack of activity could not be attributed to the 3' location of the CpG motif, since CpG ODNs with a 'control' sequence at the 5' end were immunostimulatory. All ODNs containing a suppressive motif in the 5' position also inhibited co-administered CpG ODN (Tables II and III). These findings indicate that the relative position of stimulatory and suppressive motifs determines the immunomodulatory properties of DNA.

Example 5

Suppressive ODNs Block the Development of Collagen-Induced Arthritis

This example demonstrates the ability of suppressive ODNs to block the development of collagen-induced arthritis (an animal model of rheumatoid arthritis).

Figure 17:
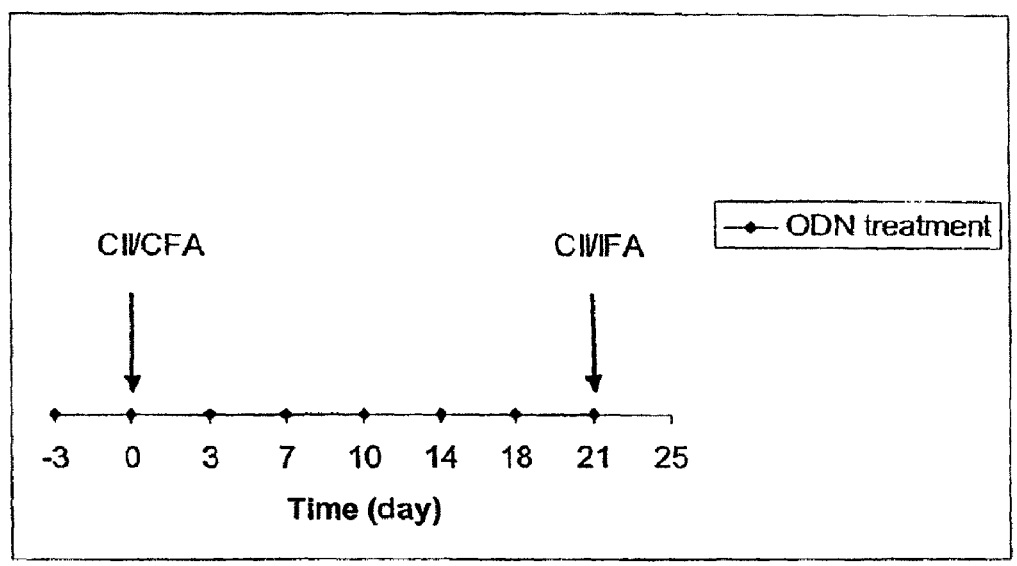
FIG. 17 is a schematic diagram of the timing of type II collagen injection and ODN administration for DBA/1 LacJ mice. Ten to twenty DBA/1 LacJ mice per group were injected with type II collagen in complete Freund's adjuvant (CII/CFA) on day 0, and with type II collagen in incomplete Freund's adjuvant (CII/IFA) on day 21 to induce arthritis. The study groups included animals treated with 200 μg of suppressive ODN A151 (SEQ ID NO: 2), control ODN 1612 (SEQ ID NO: 29) or PBS on days −3, 0, 3, 7, 10, 14, 18 and 21. The incidence of arthritis and clinical score were monitored twice weekly. Antigen-specific humoral and cellular immune responses, and local expression of pro-inflammatory cytokines, were also investigated.
Figure 18A:
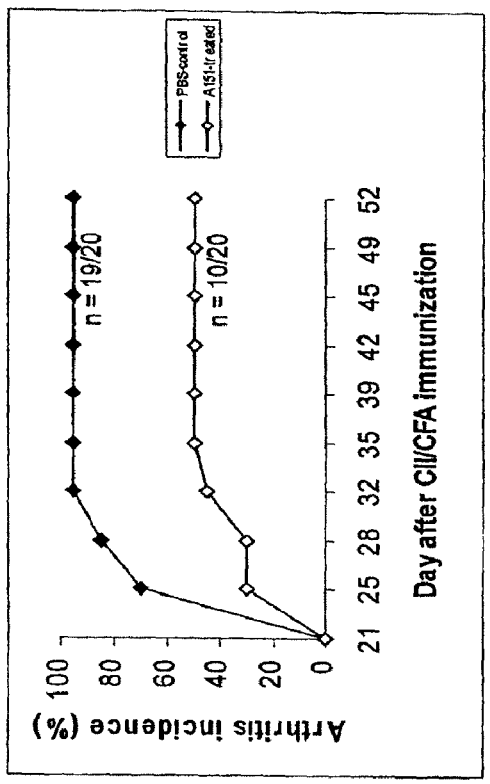
FIG. 18 is a pair of graphs showing that treatment with ODN A151 (SEQ ID NO: 2) significantly reduced both the percentage of mice that developed arthritis (FIG. 18A), and the arthritis clinical score (FIG. 18B). Standard curves were constructed by serial dilutions of a mixture of sera from arthritic mice. A single asterisk (*) indicates that $p<0.05$; a double asterisk (**) indicates that $p<0.01$, as compared with PBS-control mice.
Figure 18B:
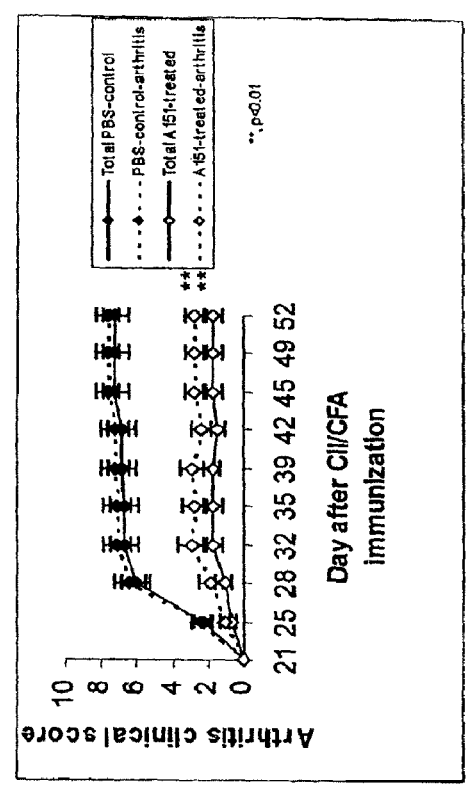

DBA/1 LacJ mice provide a murine model of human inflammation. Ten to twenty DBA/1 LacJ mice per group were injected with type II collagen in complete Freund's adjuvant (CII/CFA) on day 0, and with type II collagen in incomplete Freund's adjuvant (CII/IFA) on day 21 to induce arthritis (see FIG. 17). The study groups included animals treated with 200 μg of suppressive ODN A151 (SEQ ID NO: 2), control ODN 1612 (SEQ ID NO: 29) or PBS on days −3, 0, 3, 7, 10, 14, 18 and 21. The incidence of arthritis and clinical score were monitored twice weekly. Antigen-specific humoral and cellular immune responses, and local expression of pro-inflammatory cytokines, were also investigated. Table IV shows the incidence of arthritis and clinical score on day 56 of treatment. Treatment with ODN A151 (SEQ ID NO: 2) significantly reduced both the percentage of mice that developed arthritis (FIG. 18A), and the arthritis clinical score (FIG. 18B).

TABLE IV

Incidence of arthritis and clinical score.
Data represent results from day 56.

|  | Incidence (%) | Clinical Score |
|---|---|---|
| PBS-control | 95 (19/20) | 7.2 +/− 0.7 |
| ODN 1612-treated | 90 (9/10) | 5.9 +/− 1.1 |
| A151-treated | 50 (10/20) | 1.7 +/− .04* |

*$p < 0.05$, as compared with PBS-control or ODN 1612-treated mice.

Figure 19:
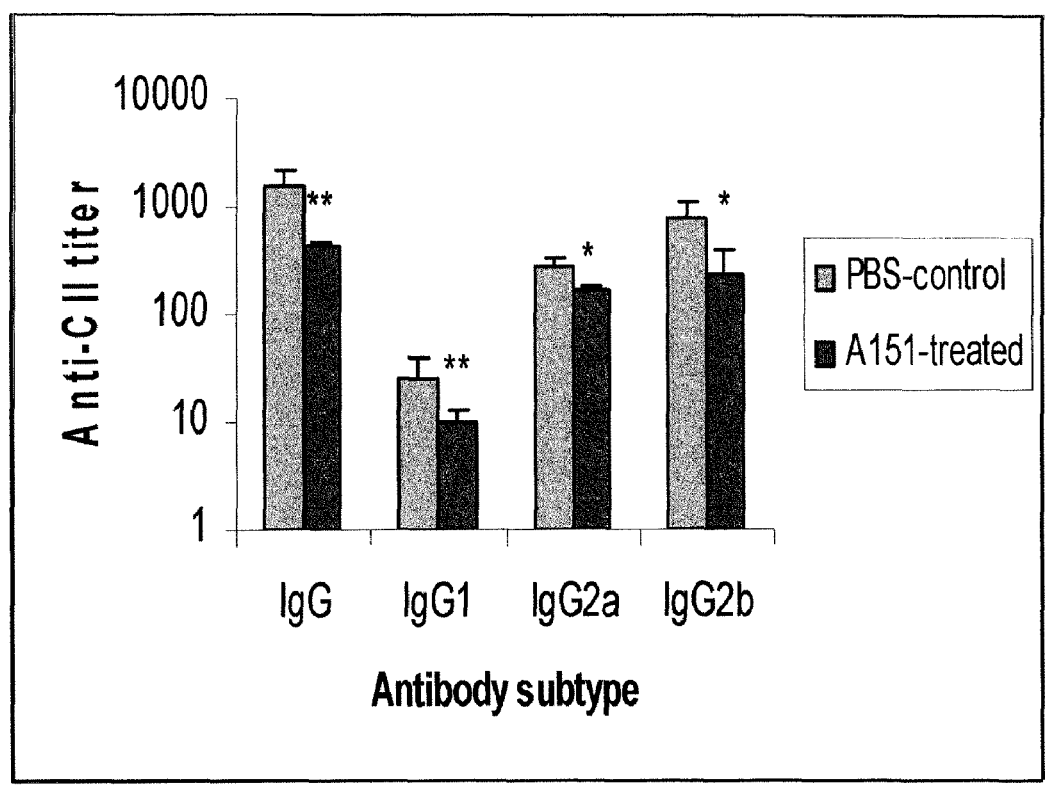
FIG. 19 is a graph showing that production of anti-type 2 collagen (CII) antibody is suppressed by A151 (SEQ ID NO: 2) treatment. Sera were collected on day 35 and assayed for IFNγ by ELISA assay, as described above. Standard curves were constructed by serial dilutions of a mixture of sera from arthritic mice. A single asterisk (*) indicates that $p<0.05$; a double asterisk (**) indicates that $p<0.01$, as compared with PBS-control mice.
Figure 20A:
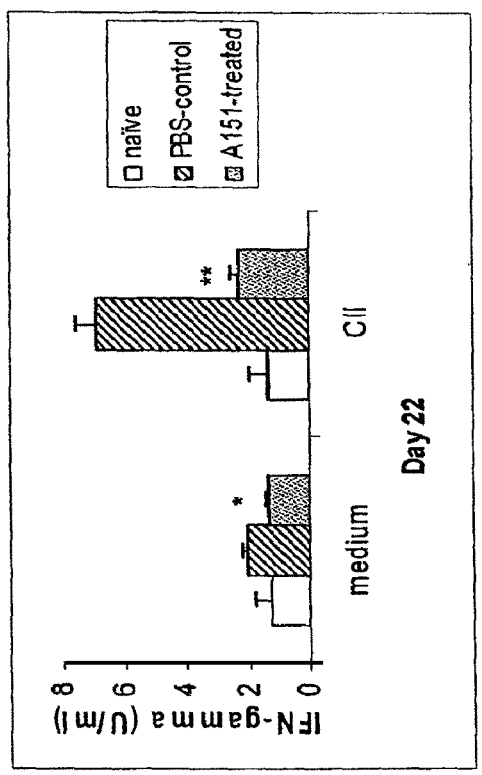
FIG. 20 is a pair of graphs showing that production of anti-CII antibody is suppressed by A151 treatment. Spleen cells from naive, PBS or A151-treated mice were isolated on day 22 (FIG. 20A) or 35 (FIG. 20B). Cells were stimulated in vitro with 50 μg/ml of CII for 72 hours and culture supernatants were assayed for IFN-gamma detection. Each group represents results from six mice (two separate experiments). A single asterisk (*) indicates that $p<0.05$; a double asterisk (**) indicates that $p<0.01$, as compared with naive or PBS-control mice.
Figure 20B:
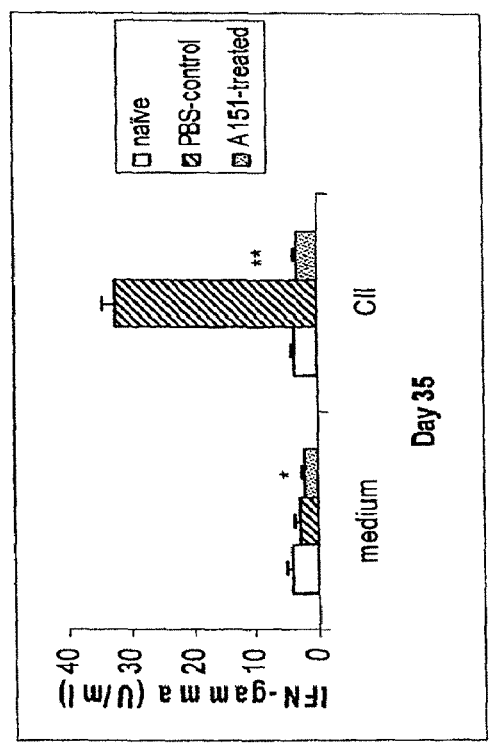

In addition, production of anti-CII antibody was suppressed by A151 treatment. In FIG. 19, sera were collected on day 35 and assayed for IFNγ by ELISA assay, as described above. Standard curves were constructed by serial dilutions of a mixture of sera from arthritic mice. In FIG. 20, spleen cells from naive, PBS or A151-treated mice were isolated on day 22 (FIG. 20A) or 35 (FIG. 20B). Cells were stimulated in vitro with 50 μg/ml of CII for 72 hours and culture supernatants were assayed for IFN-gamma detection.

Figure 21:
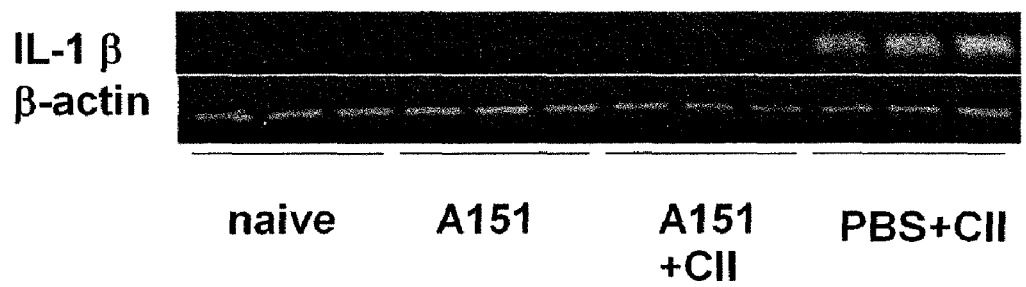
FIG. 21 is a digital image of a gel showing that in vivo (local) expression of proinflammatory cytokine is also suppressed by treatment with ODN A151. The hind paws of treated animals were removed on day 35. Total RNA was extracted from tissue homogenates, and mRNA of the pro-inflammatory cytokine IL-1β was monitored by RT-PCR. Each group contains three mice.

In vivo (local) expression of proinflammatory cytokine was also suppressed by treatment with ODN A151 (FIG. 21). The hind paws of treated animals were removed on day 35. Total RNA was extracted from tissue homogenates, and mRNA of the pro-inflammatory cytokine IL-1 β was monitored by RT-PCR.

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the following claims:

We claim:

1. An isolated oligodeoxynucleotide of 16 to 100 nucleotides in length, comprising SEQ ID NO: 1.

2. The isolated oligodeoxynucleotide of claim 1, wherein the oligodeoxynucleotide is at most 30 nucleotides in length.

3. The isolated oligodeoxynucleotide of claim 1, wherein the oligodeoxynucleotide comprises multiple guanosine-rich sequences.

4. The isolated oligodeoxynucleotide of claim 1, wherein the oligodeoxynucleotide comprises from about two to about four guanosine-rich sequences.

5. The isolated oligodeoxynucleotide of claim 1, wherein the oligodeoxynucleotide forms a G-tetrad, has a CD value of greater than about 2.9 and suppresses production of a cytokine.

6. The isolated oligodeoxynucleotide of claim 1, wherein the oligodeoxynucleotide consists of the nucleic acid sequence set forth as SEQ ID NO: 1.

7. The isolated oligodeoxynucleotide of claim 1, wherein the oligodeoxynucleotide is modified to prevent degradation.

8. The isolated oligodeoxynucleotide of claim 1, wherein the oligodeoxynucleotide has a phosphate backbone modification.

9. The isolated oligodeoxynucleotide of claim 8, wherein the phosphate backbone modification is a phosphorothioate backbone modification.

10. An oligodeoxynucleotide delivery complex comprising the oligodeoxynucleotide of claim 1 and a targeting moiety.

11. The oligodeoxynucleotide delivery complex of claim 10, wherein the targeting moiety is selected from the group consisting of a cholesterol, a virosome, a liposome, a lipid, and a target cell specific binding agent.

12. The oligodeoxynucleotide of delivery complex of claim 11, wherein the oligodeoxynucleotide and the targeting moiety are covalently linked.

13. A composition comprising the oligodeoxynucleotide of claim 1 and a pharmacologically acceptable carrier.

14. A method of decreasing the production of one or more cytokines, comprising administering to a subject a therapeutically effective amount of the oligodeoxynucleotide of claim 1 to a subject, thereby decreasing the production of the one or more cytokines, wherein the cytokine is interleukin (IL-6), IL-12, interferon (IFN)-γ or a combination thereof.

15. The method of claim 14, wherein the oligodeoxynucleotide is at most 30 nucleotides in length.

16. The method of claim 14, further comprising administering an additional anti-inflammatory or immunosuppressive agent.

17. A kit for treating inflammatory arthropathies in a subject comprising a container comprising the oligodeoxynucleotide of claim 1.

18. The kit of claim 17, wherein the oligodeoxynucleotide consists of the nucleic acid sequence set forth as SEQ ID NO: 1.

19. The kit of claim 18, further comprising a container comprising an additional anti-inflammatory, immunosuppressive, or anti-arthritis agent.

20. The composition of claim 13, comprising an effective amount of an additional anti-inflammatory, immunosuppressive, or anti-arthritis agent.

* * * * *